(12) United States Patent
Talish et al.

(10) Patent No.: US 7,410,469 B1
(45) Date of Patent: Aug. 12, 2008

(54) APPARATUS AND METHOD FOR ULTRASONICALLY AND ELECTROMAGNETICALLY TREATING TISSUE

(75) Inventors: Roger J. Talish, Hillsborough, NJ (US); Alan A. Winder, Westport, CT (US)

(73) Assignee: Exogen, Inc., Piscataway, NJ (US)

( * ) Notice: Subject to any disclaimer, the term of this patent is extended or adjusted under 35 U.S.C. 154(b) by 0 days.

(21) Appl. No.: 09/574,461

(22) Filed: May 18, 2000

Related U.S. Application Data

(60) Provisional application No. 60/135,224, filed on May 21, 1999.

(51) Int. Cl.
*A61H 1/00* (2006.01)
*A61H 5/00* (2006.01)

(52) U.S. Cl. .................. 601/2; 600/9; 600/13; 600/15; 600/439

(58) Field of Classification Search ............... 607/2, 607/3, 72, 50, 51; 601/2, 3, 4; 600/439, 600/437, 9, 13, 15, 459; 310/311
See application file for complete search history.

(56) References Cited

U.S. PATENT DOCUMENTS

| | | | |
|---|---|---|---|
| 1,063,782 A | 6/1913 | Dickey | |
| 1,604,870 A | 10/1926 | Asman | |
| 2,914,829 A | 12/1959 | Willemain | |
| 2,920,853 A | 1/1960 | Bufogle | |
| 3,117,571 A | 1/1964 | Fry et al. | |
| 3,134,451 A | 5/1964 | Hanssen | |
| 3,193,034 A | 7/1965 | Hutchinson et al. | |
| 3,241,375 A | 3/1966 | Canzoneri | |
| 3,304,036 A | 2/1967 | Davis | |

(Continued)

FOREIGN PATENT DOCUMENTS

AU 19950292 2/2000

(Continued)

OTHER PUBLICATIONS

Patent Abstracts vol. 013, n. 541 (E-854) Dec. 5,1989 Japan.

(Continued)

*Primary Examiner*—Eric F Winakur
*Assistant Examiner*—Katherine L Fernandez
(74) *Attorney, Agent, or Firm*—Kilpatrick Stockton LLP

(57) ABSTRACT

The invention relates to apparatus and method for ultrasonically and electromagnetically treating tissue to treat, for example, traumatized tissue or a bone injury. The apparatus includes at least one ultrasonic transducer assembly and at least one electromagnetic coil-assembly configured to cooperate with a placement module for placement in proximity to the treatment area. The apparatus also utilizes a portable main operating unit constructed to fit within a pouch or carrying case worn by the patient. In operation, at least one ultrasonic transducer and at least one electromagnetic coil are activated by transmitting control signals to the placement module from the main operating unit. The activation of the at least one ultrasonic transducer causes ultrasonic waves to be propagated toward the treatment area which are modulated by electrostatic and magnetic forces generated by the at least one electromagnetic coil. The activation of the at least one ultrasonic transducer and the at least one electromagnetic coil may be performed at the same time or at different times for varying periods.

32 Claims, 7 Drawing Sheets

U.S. PATENT DOCUMENTS

| | | |
|---|---|---|
| 3,310,049 A | 3/1967 | Clynes |
| 3,433,663 A | 3/1969 | Underwood |
| 3,499,437 A | 3/1970 | Balamuth |
| 3,521,225 A | 7/1970 | Kursman et al. |
| 3,550,586 A | 12/1970 | Balamuth |
| 3,575,050 A | 4/1971 | Lynnworth |
| 3,594,993 A | 7/1971 | Heyse |
| 3,664,626 A | 5/1972 | Sneller |
| 3,701,352 A | 10/1972 | Bosworth |
| 3,714,619 A | 1/1973 | Morgan et al. |
| 3,729,162 A | 4/1973 | Salvato |
| 3,760,799 A | 9/1973 | Crowson |
| 3,767,195 A | 10/1973 | Dimick |
| 3,828,769 A | 8/1974 | Mettler |
| 3,855,638 A | 12/1974 | Pilliar |
| 3,890,953 A | 6/1975 | Kraus et al. |
| 3,961,380 A | 6/1976 | Garr |
| 3,986,212 A | 10/1976 | Sauer |
| 4,037,592 A | 7/1977 | Kronner |
| 4,105,017 A | 8/1978 | Ryaby et al. |
| 4,108,165 A | 8/1978 | Kopp et al. |
| 4,127,125 A | 11/1978 | Takemoto et al. |
| 4,141,524 A | 2/1979 | Corvese, Jr. |
| 4,164,794 A | 8/1979 | Spector et al. |
| 4,170,045 A | 10/1979 | Estes |
| 4,176,664 A | 12/1979 | Kalish |
| 4,195,517 A | 4/1980 | Kalinoski et al. |
| 4,206,516 A | 6/1980 | Pilliar |
| 4,216,766 A | 8/1980 | Duykers et al. |
| 4,227,111 A | 10/1980 | Cross et al. |
| 4,229,992 A | 10/1980 | McKee et al. |
| 4,233,477 A | 11/1980 | Rice et al. |
| 4,266,532 A | 5/1981 | Ryaby et al. |
| 4,266,533 A | 5/1981 | Ryaby et al. |
| 4,269,797 A | 5/1981 | Mikiya et al. |
| 4,291,025 A | 9/1981 | Pellico |
| 4,296,753 A | 10/1981 | Goudin |
| 4,312,536 A | 1/1982 | Lloyd |
| 4,315,503 A | 2/1982 | Ryaby et al. |
| 4,315,514 A | 2/1982 | Drewes et al. |
| 4,347,645 A | 9/1982 | Iseki |
| 4,351,069 A | 9/1982 | Ballintyn et al. |
| 4,355,428 A | 10/1982 | Deloison et al. |
| 4,358,105 A | 11/1982 | Sweeney, Jr. |
| 4,361,154 A | 11/1982 | Pratt, Jr. |
| 4,365,359 A | 12/1982 | Raab |
| 4,383,533 A | 5/1983 | Lovelace et al. |
| 4,407,044 A | 10/1983 | Iseki |
| 4,410,158 A | 10/1983 | Maffel |
| 4,421,119 A | 12/1983 | Pratt, Jr. |
| 4,431,038 A | 2/1984 | Rome |
| 4,440,025 A | 4/1984 | Hayakawa et al. |
| 4,441,486 A | 4/1984 | Pounds |
| 4,446,586 A | 5/1984 | Reed et al. |
| 4,452,326 A | 6/1984 | Hanssen et al. |
| 4,467,659 A | 8/1984 | Baumoel |
| 4,476,847 A | 10/1984 | Taenzer et al. |
| 4,476,874 A | 10/1984 | Taenzer et al. |
| 4,482,942 A | 11/1984 | Blaisdell et al. |
| 4,511,921 A | 4/1985 | Harlan et al. |
| 4,530,360 A | 7/1985 | Duarte |
| 4,536,894 A | 8/1985 | Galante et al. |
| 4,542,539 A | 9/1985 | Rowe, Jr. et al. |
| 4,542,744 A | 9/1985 | Barnes et al. |
| 4,550,714 A | 11/1985 | Talish |
| 4,556,066 A | 12/1985 | Semrow |
| 4,557,148 A | 12/1985 | Akiyama |
| 4,570,487 A * | 2/1986 | Gruber .................. 73/624 |
| 4,570,640 A | 2/1986 | Barsa |
| 4,570,927 A | 2/1986 | Petrofsky et al. |
| 4,573,996 A | 3/1986 | Kwiatek et al. |
| 4,594,662 A | 6/1986 | Devaney |
| 4,612,160 A | 9/1986 | Donlevy et al. |
| 4,627,429 A | 12/1986 | Tsuk |
| 4,630,323 A | 12/1986 | Sage et al. |
| 4,644,942 A | 2/1987 | Sump |
| 4,646,725 A | 3/1987 | Moasser |
| 4,657,543 A | 4/1987 | Langer et al. |
| 4,669,483 A | 6/1987 | Hepp et al. |
| 4,677,438 A | 6/1987 | Michiguchi et al. |
| 4,680,967 A | 7/1987 | Rost |
| 4,687,195 A | 8/1987 | Potts |
| 4,689,986 A | 9/1987 | Carson et al. |
| 4,708,127 A | 11/1987 | Abdelghani |
| 4,710,655 A | 12/1987 | Masaki |
| 4,725,272 A | 2/1988 | Gale |
| 4,726,099 A | 2/1988 | Card |
| 4,763,661 A | 8/1988 | Sommer et al. |
| 4,770,184 A | 9/1988 | Greene, Jr. et al. |
| 4,774,959 A | 10/1988 | Palmer et al. |
| RE32,782 E | 11/1988 | Pratt, Jr. |
| 4,782,822 A | 11/1988 | Ricken |
| 4,787,070 A | 11/1988 | Suzuki et al. |
| 4,787,888 A | 11/1988 | Fox |
| 4,792,336 A | 12/1988 | Hlavacek et al. |
| 4,802,477 A | 2/1989 | Gabbay |
| 4,830,015 A | 5/1989 | Okazaki |
| 4,836,316 A | 6/1989 | Carnevale et al. |
| 4,855,911 A | 8/1989 | Lele et al. |
| 4,858,599 A | 8/1989 | Halpern |
| 4,867,169 A | 9/1989 | Machida et al. |
| 4,891,849 A | 1/1990 | Robinson |
| 4,905,671 A | 3/1990 | Senge et al. |
| 4,913,157 A | 4/1990 | Pratt, Jr. et al. |
| 4,917,092 A | 4/1990 | Todd et al. |
| 4,917,376 A | 4/1990 | Lo |
| 4,920,966 A | 5/1990 | Hon et al. |
| 4,926,870 A | 5/1990 | Brandenburger |
| 4,928,959 A | 5/1990 | Bassett et al. |
| 4,930,358 A | 6/1990 | Motegi et al. |
| 4,932,951 A | 6/1990 | Liboff et al. |
| 4,933,230 A | 6/1990 | Card et al. |
| 4,936,303 A | 6/1990 | Detwiler et al. |
| 4,941,474 A | 7/1990 | Pratt, Jr. |
| 4,947,853 A | 8/1990 | Hon |
| 4,979,501 A | 12/1990 | Valchanov et al. |
| 4,982,730 A | 1/1991 | Lewis, Jr. |
| 4,984,462 A | 1/1991 | Hass, Jr. et al. |
| 4,986,275 A | 1/1991 | Ishida et al. |
| 4,993,413 A | 2/1991 | McLeod et al. |
| 4,995,883 A | 2/1991 | Demane et al. |
| 5,000,183 A | 3/1991 | Bonnefous |
| 5,000,442 A | 3/1991 | Dalebout et al. |
| 5,003,965 A | 4/1991 | Talish et al. |
| 5,004,476 A | 4/1991 | Cook |
| 5,016,641 A | 5/1991 | Schwartz |
| 5,018,285 A | 5/1991 | Zolman et al. |
| 5,046,484 A | 9/1991 | Bassett et al. |
| 5,054,490 A | 10/1991 | Rossman et al. |
| 5,067,940 A | 11/1991 | Liboff et al. |
| 5,080,672 A | 1/1992 | Bellis |
| 5,088,976 A | 2/1992 | Liboff et al. |
| 5,099,702 A | 3/1992 | French |
| 5,100,373 A | 3/1992 | Liboff et al. |
| 5,103,806 A | 4/1992 | McLeod et al. |
| 5,106,361 A | 4/1992 | Liboff et al. |
| 5,107,853 A | 4/1992 | Plyter |
| 5,108,452 A | 4/1992 | Fallin |
| 5,133,420 A | 7/1992 | Smith |
| 5,134,999 A | 8/1992 | Osipov |
| 5,139,498 A | 8/1992 | Astudillo Ley |
| 5,140,988 A | 8/1992 | Stouffer et al. |
| 5,143,069 A | 9/1992 | Kwon et al. |
| 5,143,073 A | 9/1992 | Dory |

| | | | | | | |
|---|---|---|---|---|---|---|
| 5,154,189 | A | 10/1992 | Oberlander | 5,492,525 | A | 2/1996 | Gibney |
| 5,163,598 | A | 11/1992 | Peters et al. | 5,495,846 | A | 3/1996 | Uehara et al. |
| 5,172,692 | A | 12/1992 | Kulow et al. | 5,496,256 | A | 3/1996 | Bock et al. |
| 5,178,134 | A | 1/1993 | Vago | 5,501,657 | A | 3/1996 | Feero |
| 5,181,512 | A | 1/1993 | Viebach et al. | 5,507,800 | A | 4/1996 | Strickland |
| 5,184,605 | A | 2/1993 | Grzeszykowski | 5,507,830 | A | 4/1996 | DeMane et al. |
| 5,186,162 | A | 2/1993 | Talish et al. | 5,509,933 | A | 4/1996 | Davidson et al. |
| 5,191,880 | A | 3/1993 | McLeod et al. | 5,520,612 | A | 5/1996 | Winder et al. |
| 5,197,475 | A | 3/1993 | Antich et al. | 5,524,624 | A | 6/1996 | Tepper et al. |
| 5,201,766 | A | 4/1993 | Georgette | 5,526,815 | A | 6/1996 | Granz et al. |
| 5,209,221 | A | 5/1993 | Riedlinger | 5,541,489 | A | 7/1996 | Dunstan |
| 5,211,160 | A | 5/1993 | Talish et al. | 5,547,459 | A | 8/1996 | Kaufman et al. |
| 5,230,334 | A | 7/1993 | Klopotek | 5,556,372 | A | 9/1996 | Talish et al. |
| 5,230,345 | A | 7/1993 | Curran et al. | 5,578,060 | A * | 11/1996 | Pohl et al. ................. 607/3 |
| 5,230,646 | A | 7/1993 | Thorup | 5,615,466 | A | 4/1997 | Safari et al. |
| 5,230,921 | A | 7/1993 | Waltonen et al. | 5,626,554 | A | 5/1997 | Ryaby et al. |
| 5,235,981 | A | 8/1993 | Hascoet et al. | 5,626,630 | A | 5/1997 | Markowitz et al. |
| 5,254,123 | A | 10/1993 | Bushey | 5,630,837 | A | 5/1997 | Crowley |
| 5,259,384 | A | 11/1993 | Kaufman et al. | D380,440 | S | 7/1997 | Talish et al. |
| 5,269,306 | A | 12/1993 | Warnking et al. | 5,644,093 | A | 7/1997 | Wright et al. |
| 5,273,028 | A | 12/1993 | McLeod et al. | 5,648,941 | A | 7/1997 | King |
| 5,280,728 | A | 1/1994 | Sato et al. | 5,656,016 | A | 8/1997 | Ogden |
| 5,284,143 | A | 2/1994 | Rattner | 5,665,141 | A | 9/1997 | Vago |
| 5,285,788 | A | 2/1994 | Arenson et al. | 5,680,863 | A | 10/1997 | Hossack et al. |
| 5,295,931 | A | 3/1994 | Dreibelbis et al. | 5,690,608 | A | 11/1997 | Watanabe et al. |
| 5,301,683 | A | 4/1994 | Durkan | 5,691,960 | A | 11/1997 | Gentilman et al. |
| 5,307,284 | A | 4/1994 | Brunfeldt et al. | 5,699,803 | A | 12/1997 | Carodiskey |
| 5,309,898 | A | 5/1994 | Kaufman et al. | 5,702,353 | A | 12/1997 | Guzzini et al. |
| 5,310,408 | A | 5/1994 | Schryver et al. | 5,702,389 | A | 12/1997 | Taylor et al. |
| 5,314,401 | A | 5/1994 | Tepper | 5,706,818 | A | 1/1998 | Gondo |
| 5,316,000 | A | 5/1994 | Chapelon et al. | 5,708,236 | A | 1/1998 | Shaanan et al. |
| 5,318,561 | A | 6/1994 | McLeod et al. | 5,721,400 | A | 2/1998 | Haraldsson et al. |
| 5,318,779 | A | 6/1994 | Hakamatsuka et al. | 5,725,482 | A | 3/1998 | Bishop |
| 5,322,067 | A | 6/1994 | Prater et al. | 5,728,095 | A | 3/1998 | Taylor et al. |
| 5,323,769 | A | 6/1994 | Bommannan et al. | 5,730,705 | A | 3/1998 | Talish et al. |
| 5,327,890 | A | 7/1994 | Matura et al. | 5,738,625 | A | 4/1998 | Gluck |
| 5,330,481 | A | 7/1994 | Hood et al. | 5,741,317 | A | 4/1998 | Ostrow |
| 5,330,489 | A | 7/1994 | Green et al. | 5,743,862 | A | 4/1998 | Izumi |
| 5,334,214 | A | 8/1994 | Putnam | 5,752,924 | A | 5/1998 | Kaufman et al. |
| 5,339,804 | A | 8/1994 | Kemp | 5,755,746 | A | 5/1998 | Lifshey et al. |
| 5,340,510 | A | 8/1994 | Bowen | 5,762,616 | A | 6/1998 | Talish |
| 5,351,389 | A | 10/1994 | Erickson et al. | 5,779,600 | A | 7/1998 | Pape |
| 5,363,850 | A | 11/1994 | Soni et al. | 5,785,656 | A | 7/1998 | Chiabrera et al. |
| 5,366,465 | A | 11/1994 | Mirza | 5,818,149 | A | 10/1998 | Safari et al. |
| 5,367,500 | A | 11/1994 | Ng | 5,829,437 | A | 11/1998 | Bridges |
| 5,368,044 | A | 11/1994 | Cain et al. | 5,843,741 | A | 12/1998 | Wong et al. |
| 5,376,065 | A | 12/1994 | McLeod et al. | 5,856,622 | A | 1/1999 | Yamamoto et al. |
| 5,380,269 | A | 1/1995 | Urso | 5,868,649 | A | 2/1999 | Erickson et al. |
| 5,386,830 | A | 2/1995 | Powers et al. | 5,871,446 | A | 2/1999 | Wilk |
| 5,393,296 | A | 2/1995 | Rattner | 5,886,302 | A | 3/1999 | Germanton et al. |
| 5,394,877 | A | 3/1995 | Orr et al. | 5,891,143 | A | 4/1999 | Taylor et al. |
| 5,394,878 | A | 3/1995 | Frazin et al. | 5,899,425 | A | 5/1999 | Corey Jr. et al. |
| 5,398,290 | A | 3/1995 | Brethour | 5,904,659 | A | 5/1999 | Duarte et al. |
| 5,400,795 | A | 3/1995 | Murphy et al. | 5,906,580 | A | 5/1999 | Kline-Schoder et al. |
| 5,405,389 | A | 4/1995 | Conta et al. | 5,954,675 | A | 9/1999 | Dellagatta |
| 5,409,446 | A | 4/1995 | Rattner | 5,957,814 | A | 9/1999 | Eschenbach |
| RE34,959 | E | 5/1995 | Potts | 5,962,790 | A | 10/1999 | Lynnworth et al. |
| 5,413,550 | A | 5/1995 | Castel | 5,971,984 | A | 10/1999 | Taylor et al. |
| 5,415,167 | A | 5/1995 | Wilk | 5,997,490 | A | 12/1999 | McLeod et al. |
| 5,417,215 | A | 5/1995 | Evans et al. | 6,019,710 | A | 2/2000 | Dalebout et al. |
| 5,424,550 | A | 6/1995 | Kawano et al. | 6,022,349 | A | 2/2000 | McLeod et al. |
| 5,425,954 | A | 6/1995 | Thompson et al. | 6,028,066 | A | 2/2000 | Unger |
| 5,431,612 | A | 7/1995 | Holden | 6,030,386 | A | 2/2000 | Taylor et al. |
| 5,434,827 | A | 7/1995 | Bolorforosh | 6,048,323 | A | 4/2000 | Hon |
| 5,441,051 | A | 8/1995 | Hileman et al. | 6,050,943 | A * | 4/2000 | Slayton et al. .............. 600/439 |
| 5,441,058 | A | 8/1995 | Fareed | 6,061,597 | A | 5/2000 | Rieman et al. |
| 5,448,994 | A | 9/1995 | Iinuma | 6,065,350 | A | 5/2000 | Hill et al. |
| 5,460,595 | A | 10/1995 | Hall et al. | 6,068,596 | A * | 5/2000 | Weth et al. ................. 600/437 |
| 5,466,215 | A | 11/1995 | Lair et al. | 6,080,088 | A | 6/2000 | Petersen et al. |
| 5,468,220 | A | 11/1995 | Sucher | 6,082,181 | A | 7/2000 | Greenwood |
| 5,476,438 | A | 12/1995 | Edrich et al. | 6,086,078 | A | 7/2000 | Ferez |
| 5,478,306 | A | 12/1995 | Stoner | 6,088,613 | A | 7/2000 | Unger |
| 5,484,388 | A | 1/1996 | Bassett et al. | 6,093,135 | A | 7/2000 | Huang |

| | | | |
|---|---|---|---|
| 6,105,431 A | 8/2000 | Duffill et al. | |
| 6,165,144 A | 12/2000 | Talish et al. | |
| 6,179,797 B1 * | 1/2001 | Brotz | 601/150 |
| 6,190,336 B1 | 2/2001 | Duarte et al. | |
| 6,206,843 B1 | 3/2001 | Iger et al. | |
| 6,213,958 B1 | 4/2001 | Winder | |
| 6,234,975 B1 | 5/2001 | McLeod et al. | |
| 6,234,990 B1 | 5/2001 | Rowe et al. | |
| 6,258,020 B1 | 7/2001 | Lopez | |
| 6,261,221 B1 * | 7/2001 | Tepper et al. | 600/14 |
| 6,261,249 B1 | 7/2001 | Talish et al. | |
| 6,264,650 B1 | 7/2001 | Hovda et al. | |
| 6,273,864 B1 | 8/2001 | Duarte | |
| 6,311,402 B1 | 11/2001 | Brandl et al. | |
| 6,322,527 B1 | 11/2001 | Talish | |
| 6,355,006 B1 | 3/2002 | Ryaby et al. | |
| 6,360,027 B1 | 3/2002 | Hossack et al. | |
| 6,394,955 B1 | 5/2002 | Perlitz | |
| 6,397,683 B1 | 6/2002 | Hagenmeyer et al. | |
| 6,406,443 B1 | 6/2002 | Talish | |
| 6,436,060 B1 | 8/2002 | Talish | |
| 6,443,898 B1 | 9/2002 | Unger | |
| 6,464,687 B1 | 10/2002 | Ishikawa et al. | |
| 6,503,214 B1 | 1/2003 | Talish | |
| 6,524,261 B2 | 2/2003 | Talish et al. | |
| 6,685,656 B1 | 2/2004 | Duarte et al. | |
| 6,733,468 B2 | 5/2004 | Talish | |
| 6,932,308 B2 | 8/2005 | Talish et al. | |
| 6,960,173 B2 | 11/2005 | Babaev | |
| 7,108,663 B2 | 9/2006 | Talish | |
| 7,211,060 B1 | 5/2007 | Talish | |
| 2002/0016557 A1 | 2/2002 | Duarte | |
| 2002/0068871 A1 | 6/2002 | Mendlein et al. | |
| 2002/0103448 A1 | 8/2002 | Babaev | |
| 2002/0115960 A1 | 8/2002 | Redding, Jr. | |
| 2002/0156400 A1 | 10/2002 | Babaev | |
| 2002/0190136 A1 | 12/2002 | Babaev | |
| 2003/0013956 A1 | 1/2003 | Michaeli | |
| 2003/0153846 A1 | 8/2003 | Talish | |
| 2003/0153849 A1 | 8/2003 | Huckle | |
| 2004/0127790 A1 | 7/2004 | Lang et al. | |
| 2005/0096548 A1 | 5/2005 | Talish | |
| 2006/0106424 A1 | 5/2006 | Bachem | |

FOREIGN PATENT DOCUMENTS

| | | |
|---|---|---|
| CA | 1328485 | 4/1994 |
| DE | 3639263 A1 | 6/1987 |
| DE | 4111055 A1 | 10/1991 |
| DE | 19613425 | 1/1997 |
| DE | 29811185 U1 | 10/1998 |
| EP | 0 181 506 A2 | 5/1986 |
| EP | 331 348 A1 | 9/1989 |
| EP | 0 536 875 A1 | 4/1993 |
| EP | 0 679 371 A1 | 11/1995 |
| EP | 0 695 559 | 2/1996 |
| EP | 0 965 839 A1 | 12/1999 |
| GB | 2156983 A | 10/1985 |
| GB | 2277448 A | 11/1994 |
| GB | 2 303 552 A | 2/1997 |
| JP | SHO 62-47359 | 3/1987 |
| JP | HEI 4-82567 | 3/1992 |
| JP | HEI 4-82568 | 3/1992 |
| JP | HEI 4-82569 | 3/1992 |
| JP | HEI 5-269159 | 10/1993 |
| WO | WO 85/03449 | 8/1985 |
| WO | WO88/00845 | 2/1988 |
| WO | WO88/02250 | 4/1988 |
| WO | WO90/06720 | 6/1990 |
| WO | WO94/13411 | 6/1994 |
| WO | WO95/03744 | 2/1995 |
| WO | WO95/33416 | 12/1995 |
| WO | WO96/25112 | 8/1996 |
| WO | WO96/25888 | 8/1996 |
| WO | WO97/33649 | 9/1997 |
| WO | WO98/10729 | 3/1998 |
| WO | WO98/34578 | 8/1998 |
| WO | WO98/47570 | 10/1998 |
| WO | WO99/18876 | 4/1999 |
| WO | WO99/22652 | 5/1999 |
| WO | WO99/48621 | 9/1999 |
| WO | WO99/56829 | 11/1999 |
| WO | WO99/58080 | 11/1999 |
| WO | WO 00/03663 | 1/2000 |
| WO | WO 00/28925 | 5/2000 |
| WO | WO 00/67846 | 11/2000 |
| WO | WO 00/71207 | 11/2000 |
| WO | WO 00/76406 | 12/2000 |

OTHER PUBLICATIONS

Abstract, (Proceedings of the 11th Int'l. Conference on Medical and Biological Engineering) "Ultrasonic Stimulation of Fracture Healing", 1976.

Abstract, (Proceedings of the III Congress on Biomedical Engineering) "Ultrasonic Action on Callus Formation in Bones", 1975.

Abstract, (Proceedings of the IV Brazilain Congress on Biomedical Engineering) "Ultrasound in the Treatment of Fractures", 1977.

ASTM Designation: D790M-93 Metric, "Standard Test Methods for flexural Properties of Unreinforced and Reinforced Plastics and Electrical Insulating Materials [Metric]", pp. 176-184, (Dec. 1993).

ASTM Designation: C1161-90, "Standard Test Method for Flexural Strength of Advanced Ceramics at Ambient Temperature," pp. 324-330.(Feb. 1991).

Brochure: "The Science Behind the Technology," distributed by Smith & Nephew for EXOGEN. (no date).

Arai et al., "The Effect of Ultrasound Stimulation on Disuse Osteoporosis", BRAGS 17, 1993.

Berridge, M.J., "Inositol Triphosphate and Calcium Signaling", *Nature* (1993), 361:315-325.

Clarke, P.R. et al., "Physical and Chemical Aspects of Ultrasonic Disruption of Cells", *JASA* (1969), 47(2): 649-653.

Duarte, L.R., "The Stimulation of Bone Growth by Ultrasound", *Arch. Orthop. Trauma Surg* (1983), 101: 153-159.

Dyson, M., "Therapeutic Applications of Ultrasound", *Biological Effects of Ultrasound* (1985), Nyborg, W.L. and Ziskin. M.C., eds; Churchill Livingstone Inc., New York; Chapter 11.

Goodship, A.E. et al., "The Influence of Induced Micromovement Upon the Healing of Experimental Tibial Fractures", *J. Bone and Joint Surg.* (1985), 67-B(4): 650-655.

Heckman, J.D. et al., "Acceleration of Tibial Fracture Healing by Non-Invasive Low-Intensity Pulsed Ultrasound", *J. Bone and Joint Surg.* (1994), 76-A(1): 26-34.

Hill, C.R., "Ultrasonic Exposure Thresholds for Changes in Cells and Tissues", *JASA* (1972), 52(2): 667-672.

Howkins, S.D., "Diffusion Rates and the Effect of Ultrasound", *Ultrasonics* (1969), 129-130.

Kristiansen, T.K. et al., "Accerlated Healing of Distal Radial Fractures with the Use of Specific, Low-Intensity Ultrasound", *J. Bone and Joint Surg.* (1997), 79-A(7) 961-973.

Maurice Hilario, "Low-Intensity Ultrasound Radiation in the Tissue Repair of Trophic Leg Ulcers", 1983, University of Sao Paulo, pp. 1-125.

Pethica, B.A., et al., Abstract, Biological Repair and Growth Society, Jun. 1998.

Pheonix (Business Wire), Jul. 8, 1997 via CompanyLink—OrthoLogic Corp.

Pilla, A.A. et al., "Non-Invasive Low-Intensity Ultrasound Accelerates Bone Repair: Rabbit Fiubla Model and Human Colles' and Tibial Fractures", *Annual Intl. Conference of IEEE-EMBS Proceedings* (1990), 12:1573-1574.

Ter Haar, G., et al., "Basic Physics of Therapeutic Ultrasound", *Physiotherapy* (1987), 73(3): 110-113.

Wallace, A.L.; Draper E.R.C.; Strachan, R.K.; McCarthy, I.D.; Hughes, S.P.F., "The Vascular Response to Fracture Micromovement", *Clinical Orthopaedics and Related Research* (1994), 301: 281-290.

Wang, S.J. et al., "Low-Intensity Ultrasound Treatment Increases Strength in a Rat Femoral Fracture Model", *J. Ortho Research* (1994), 12: 40-47.

Webster, D.F.et al., "The Role of Ultrasound-Induced Cavitation in the 'In Vitro' Stimulation of Collagen Synthesis in Human Fibroblasts", *Ultrasonics* (1980), 33-37.

Yang, K.H. et al., "Exposure to Low-Intensity Ultrasound Treatment Increases Aggrecan Gene Expression in a Rat Femur Fracture Model", *J. Ortho Research* (1996), 14:802-809.

Treatment of Osteochondral Defects in Rabbits with SAFHS—Parts I and II, EX1095-01R, EX1096-01R.

Treatment of Osteochondral Defects in Rabbits with SAFHS—Part III, EX1097-01R (Aug. 26, 1997).

Cook, Stephen and L. Patron, "Treatment of Osteorchondral Defects in Rabbits with SAFHS—A Mosaicplasty Model"—Final Report, EX1098-04R (Aug. 12, 1999).

Acoustic Emission—An Update, by Arthur E. Lord, Jr., 1981, Physical Acoustics, vol. XV, pp. 295-360.

Acoustic Emission and Diagnosis of Osteoporosis, by S. Hanagud, G. T. Hannon and R. Clinton, 1974, Ultrasonic Symposium Proceedings (IEEE), pp. 77-81.

Acoustic Emission in Bone Substance, by S. Hanagud, R.G. Clinton and J.P. Lopez, 1973, Biomechanics Symposium Proceedings (ASME), pp. 79-81.

Acoustic Emission Inspection, by Adrian A. Pollock, 1992, ASM Handboook, vol. 17, Nondestructive Evaluation and Quality Control, pp. 278-293.

Acoustic Emission Techniques in the Development of a Diagnostic Tool for Osteoporosis, by S. Hanagud and R. G. Clinton, 1975, Ultrasonic Symposium Proceedings (IEEE), pp. 41-45.

Application of an intelligent signal processing system to acoustic emission analysis, by Igo Grabec and Wolfgang Sachse, Mar. 1989, Acoustic Society of America, pp. 787-791.

Application of correlation techniques for localization of acoustic emission sources, by I. Grabec, 1978, IPC Business Press Ltd., pp. 111-115.

Cornejo, et al, "Large-Area Flexible-Array Piezoelectric Ceramic/Polymer composite Transducer for Bone Healing Acceleration," presented at ISAFXI, Montreux, Switzerland (1998).

Clough, R. and J. Simmons, "Theory of Acoustic Emission," Metallurgy Division, national Bureau of Standards. no date.

Fritton, et al., "Whole-Body Vibration in the Skeleton: Development of a Resonance-Based Testing Device," *Annals of Biomedical Engineering*, vol. 25, pp. 831-839 (1997).

Goodship, et al., "Low magnitude high frequency mechanical stimulation of endochondral bone repair" 43rd Annual Meeting Orthopeadic Research Society, vol. 22, Sec. 1, pp. 9-13 (1997).

J. Kenwright, et al., "Controlled Mechanical Stimulation in the Treatment of Fibial Fractures," Orthopedics, Clinical Orthopedics and Related Research (1989) 241:36-47.

Jankovich, "The Effects of Mechanical Vibration on Bone Development in the Rat," *J. Biomechanics*, 1972, vol. 5, pp. 241-250.

Ko, Preform Fiber Architecture for Ceramic-Matrix Composites, Ceramic Bulletin, vol. 68, No. 2, pp. 401-414(1989).

Newnham, et al., Connectivity and Piezoelectric-Pyroelectric Composites, Med. Res. Bull., vol. 13, pp. 525-536 (1978).

Pauer, Flexible Piezoelectric Material, pp. 1-5, no date.

Powell, et al., "A Performance Appraisal of Flexible Array Structures Using a Facet Ensemble Scattering Technique," *1991 Ultrasonic Symposium*, pp. 753-766.

Powell, et al., Flexible Ultrasonic Transducer Arrays for Nondestructive Evaluation Applications—Part I: The Theoretical Modeling Approach, "*IEEE Transactions on Ultrasonics, Ferroelectrics, and Frequency Control*," vol. 43, No. 3, May 1996, pp. 385-392.

Powell, et al., "Flexible Ultrasonic Transducer Arrays for Nondestructive Evaluation Applications—Part II: Performance Assessment of different Array Configurations," *IEEE Transactions on Ultrasonics, Ferroelectrics, and Frequency Control*, vol. 43, No. 3, May 1996, pp. 393-402.

Sarvazyan, "Some General Problems of Biological Action of Ultrasound," IEEE Transactions on Sonics and Ultrasonics, vol. 30, No. 1, Jan. 1983.

Ultrasound as a Tool for Investigating Bone: Fundamental Principles and Perspectives for Use in Osteoporosis, by J. Bloch, 1993, Expanson Scientifique Francaise.

Y. Qin, et al., "Correlation of In Vivo Bone Adaptation and Mechanical Parameters Using Low Magnitude, High Frequency Loading," 41st Annual Meeting Orthopaedic Research Soc., vol. 20—Sec. 1, Feb. 13-16 (1955).

Bascom, "Other Continuous Fibers," 118/Constitutent Material Form.

Bascom, "Other Discontinuous Forms," 120/Constituent Material Forms.

Cass, "Fabrication of Continuous Ceramic Fiber by the Viscous Suspension Spinning Process," *Ceramic Bulletin*, vol. 70, No. 3, pp. 424-429 (1991).

"Development of Flexible Pieoelectric Transducers and Matching Layers for EXOGEN Incorporated," Final Report, Covering Period Apr. 1, 1997 to Feb. 28, 1998, Rutgers University.

Grewe, et al., "Acoustic Properties of Particle Polymer Composite for Ultrasonic Transducer Backing Applications," *IEEE*, (1990).

Grewe, Martha G., "Acoustic Matching And Backing Layer for Medical Ultrasonic Transducers," A Thesis in Solid State Science, The Pennsylvania State University; (May 1989), The Center for Ceramics Research, Rutgers.

Gururaja, T., "Piezoelectric Composite Materials for Ultrasonic Transducer Applications," A Thesis in Solid State Science, The Pennsylvania State University, May 1984.

Gururaja, "Piezoelectrics for Medical Ultrasonic Imaging," *Am. Ceram. Soc. Bull.*, vol. 73, No. 5, pp. 50-55 (May 1994).

Hall, et al., "The design and evaluation of ultrasonic arrays using 1-3 connectivity composites," *SPIE*, pp. 216-227, vol. 1733 (1992).

Pilla, et al., "Non-Invasive Low-Intensity Pulsed Ultrasound Accelerates Bone Healing in the Rabbit," *Journal of Orthopaedic Trauma*, vol. 4, No. 3, pp. 246-253 (1990).

Safari, "Development of piezoelectric composites for transducers," *J. Phys.France*, 4:1129-1149 (1994).

Selfridge, "Approximate Material Properties in Isotropic Materials," *IEEE Transactions on Sonics and Ultrasonics*, May 9, 1985).

Souquet, et al., "Design of Low-Loss Wide-Band Ultrasonic Transducers for Noninvasive Medical Application," *IEEE Transactions on Sonics and Ultrasonics*, pp. 75-81, vol. SU-26, No. 2, Mar. 1979.

Waller, et al., "Poling of Lead Zirconate Titanate Ceramics and Flexible Piezoelectric Composites by the Corona Discharge Technique," *J. Am. Ceram. Soc.*, 72(2):322-24 (1989).

Winder, Alan, "Synthetic Structural Imaging and Volume Estimation of Biological Tissue Organs,",Acoustic Sciences Associates, Dec. 1995.

Winder, Alan, "Acoustic Emission Monitoring for the Detection, Localization and Classification of Metabolic Bone Disease," Acoustic Sciences Associates, Dec. 1995.

Wu and Cubberly, "Measurement of Velocity and Attenuation of Shear Waves in Bovine Compact Bone Using Ultrasonic Spectroscopy," Med. & Biol., vol. 23, No. 1,129-134, 1997.

Tavakoli and Evans , 1992 (no other information available at this time).

McLeod, et al., "Improved Postural Stability Following Short Term Exposure to Low Level Whole Body Vibration," 44th Annual Meeting, Orthopaedic Research Society, Mar. 16-19, 1998, New Orleans, Louisiana, p. 89-15.

Phoenix (Business Wire), Jul. 8, 1997 via CompanyLink—OrthoLogic Corp.

Pilgrim, et al., An Extension of the Composite Nomenclature Scheme, Med. Res. Bull., vol. 22, pp. 877-894 (1987).

"Reflex Sympathetic Dystrophy, Does RSD Exist?" www.arbon.com (Jun. 04, 1997).

"Reflex Sympathetic Dystrophy: The Pain That Doesn't Stop," tcc.cc.nc.us (Jun. 04, 1997).

RSDnet.org "Reflex Sympathetic Dystrophy," www.rsdnet.org (Jun. 04, 1997).

Tavakoli and Evans , "The Effect of Bone Structure on Ultrasonic Attenuation and Velocity," *Ultrasonics*, vol. 30, No. 6 (1992).

Caplan, et al., Clinical Orthopaedics and Related Research, No. 342:245-269 (1997).

Moran, et al., "The Journal of Bone Surgery," 74-B:659-667 (1992).

Photographs of Vibration Platform Built by Julio Tous, Universitat Ramon Llull, Barcelona, Spain (7 pages, 2002).

Photographs of Excercise Ergometer Developed by Biodex Medical Systems, Shirley, New York (03 pages, 2002).

"Generation of Electric Potentials by Bona In Response to Mechanical Stress," *Science Magazine*, 137, 1063-1064 (Sep. 28, 2002).

Pethica, B.A., et al., Abstract, Biological Repair and Growth Society, Jun. 1998.

Goodship, et al., "Low magnitude high frequency mechanical stimulation of endochondral bone repair" 43$^{rd}$ Annual Meeting Orthopeadic Research Society, vol. 22, Sec. 1, Feb. 9-13 (1997).

Y. Qin, et al., "Correlation of In Vivo Bone Adaptation and Mechanical Parameters Using Low Magnitude, High Frequency Loading," 41$^{st}$ Annual Meeting Orthopaedic Reseach Soc., vol. 20 - Sec. 1, Feb. 13-16 (1955).

Grewe, et al., "Acoustic Properties of Particle Polymer Composite for Ultrasonic Transducer Backing Applications," *IEEE*, (1990).

Wu and Cubberly, "Measurement of Velocity and Attenuation of Shear Waves in Bovine Compact Bone Using Ultrasonic Spectroscopy," Med. & Biol., vol. 23, No. 1, 129-134, 1997.

Pilla, et al., "Non-Invasive Low-Intensity Pulsed Ultrasound Accelerates Bone Healing in the Rabbit," *Journal of Orthopaedic Trauma*, vol. 4, No. 3, pp. 246-253 (1990).

Bascom, "Other Continuous Fibers," 118/Constitutent Material Form.

Bascom, "Other Discontinuous Forms," 120/Constituent Material Forms.

Niemczewaki, B., "A Comparison of Ultrasonic Cavitation Intensity in Liquids," *Ultrasonics*, May 1980, pp. 107-110.

\* cited by examiner

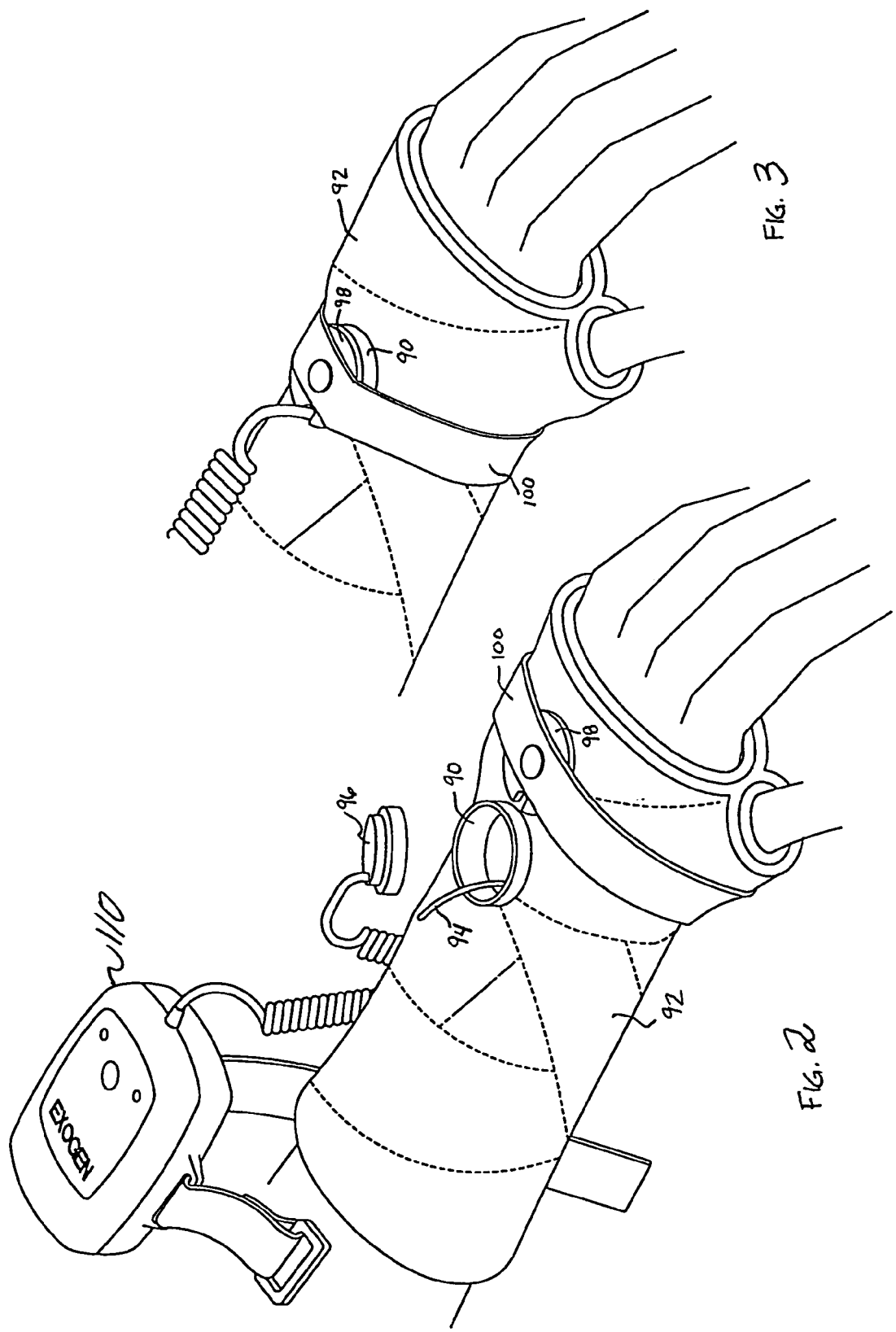

FIG. 5A
FIG. 5B
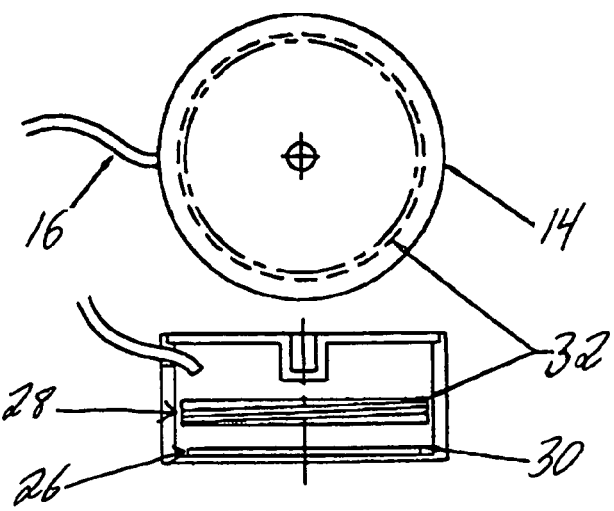
FIG. 6A
FIG. 6B
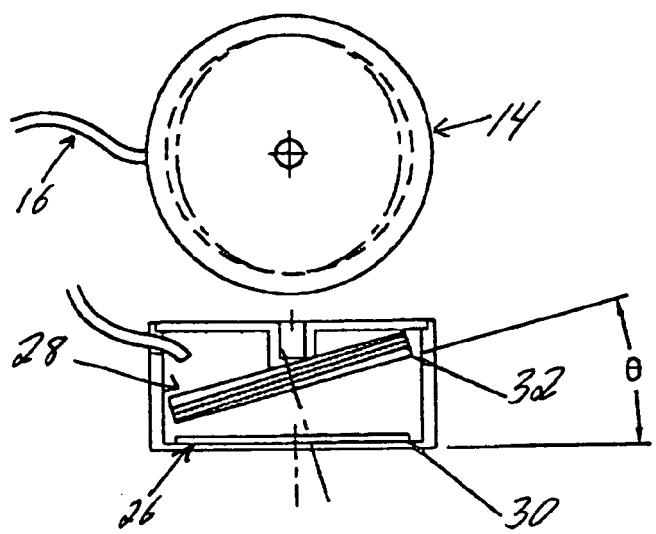
FIG. 7A
FIG. 7B
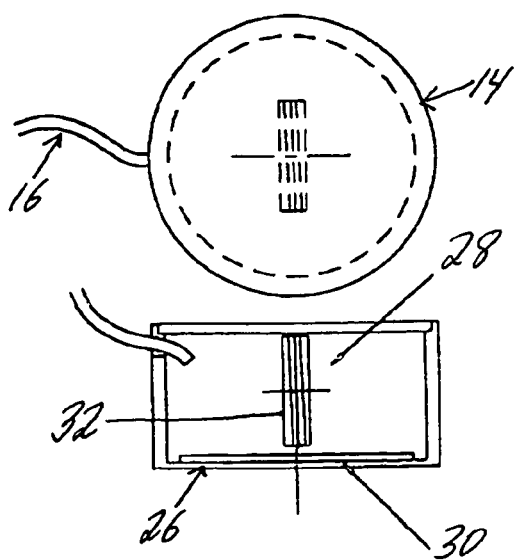

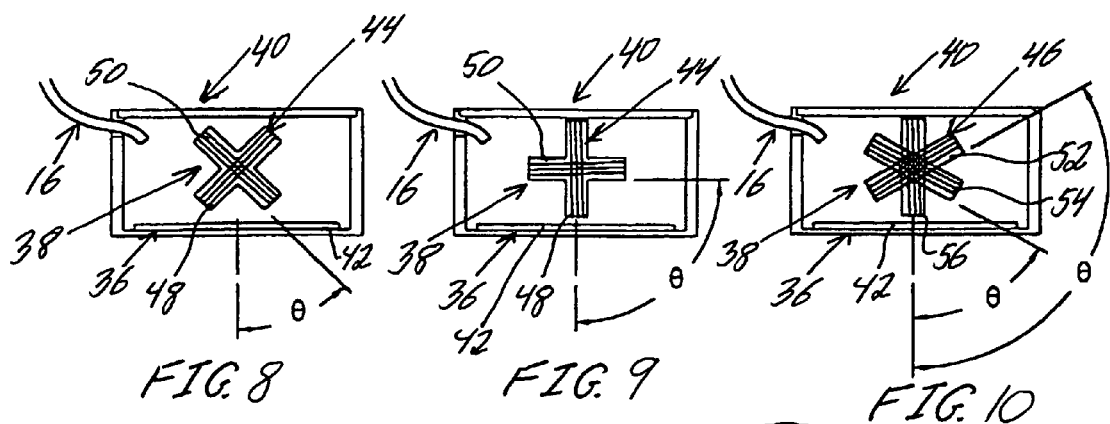
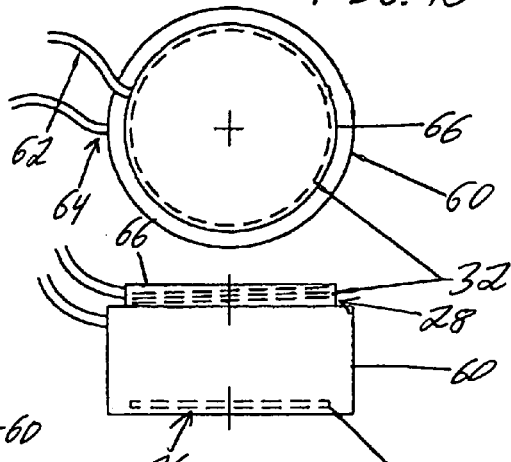
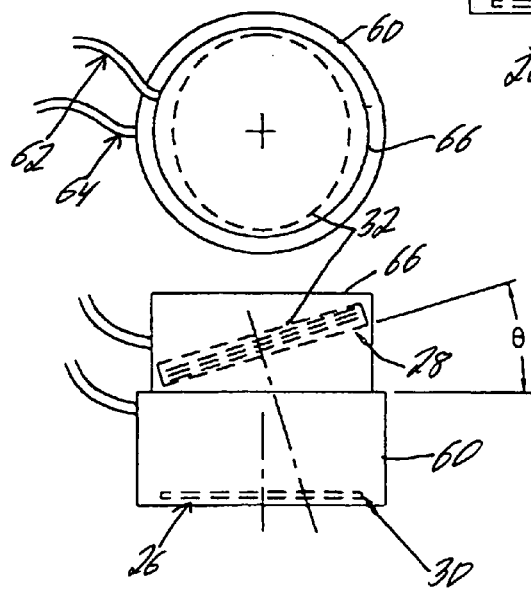

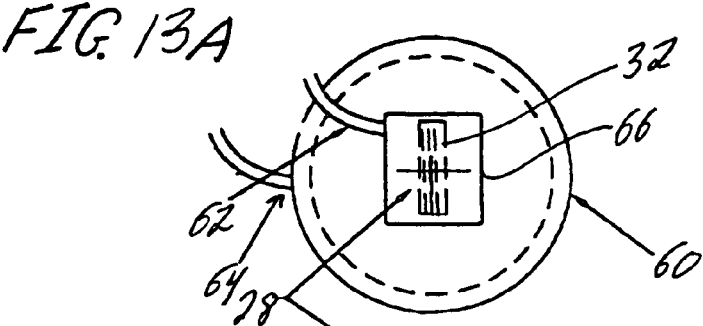
FIG. 13A
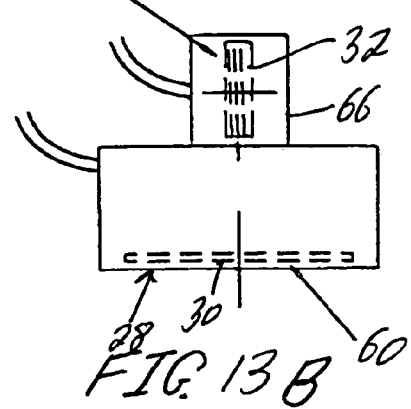
FIG. 13B
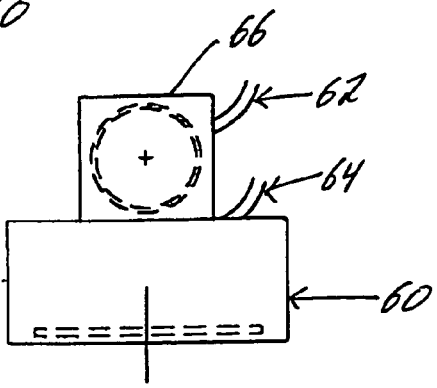
FIG. 13C
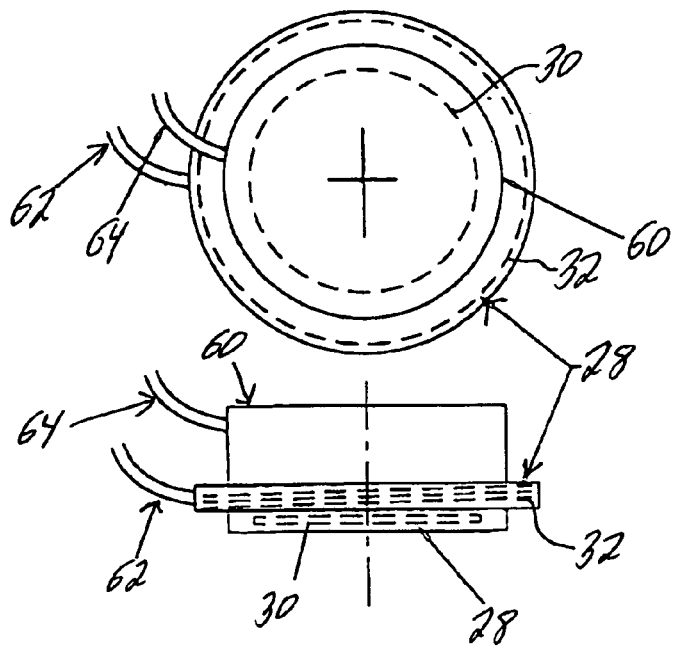
FIG. 14A
FIG. 14B

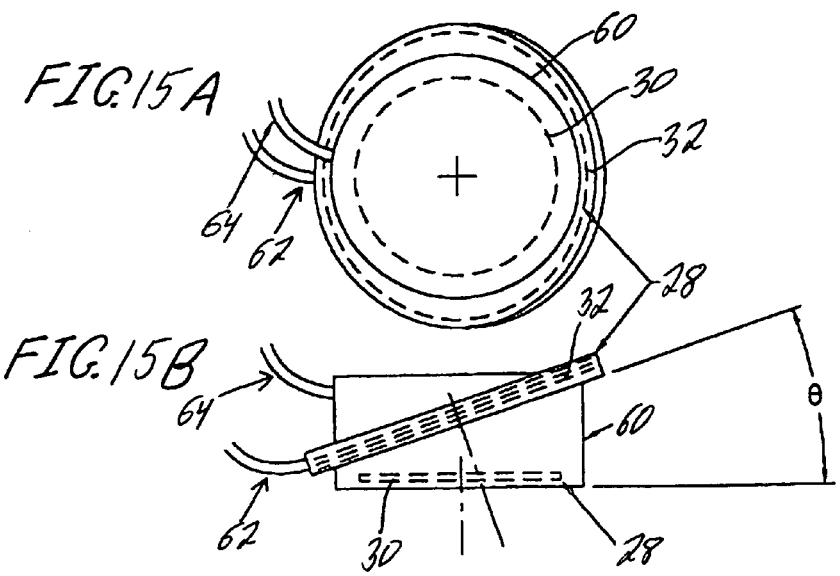
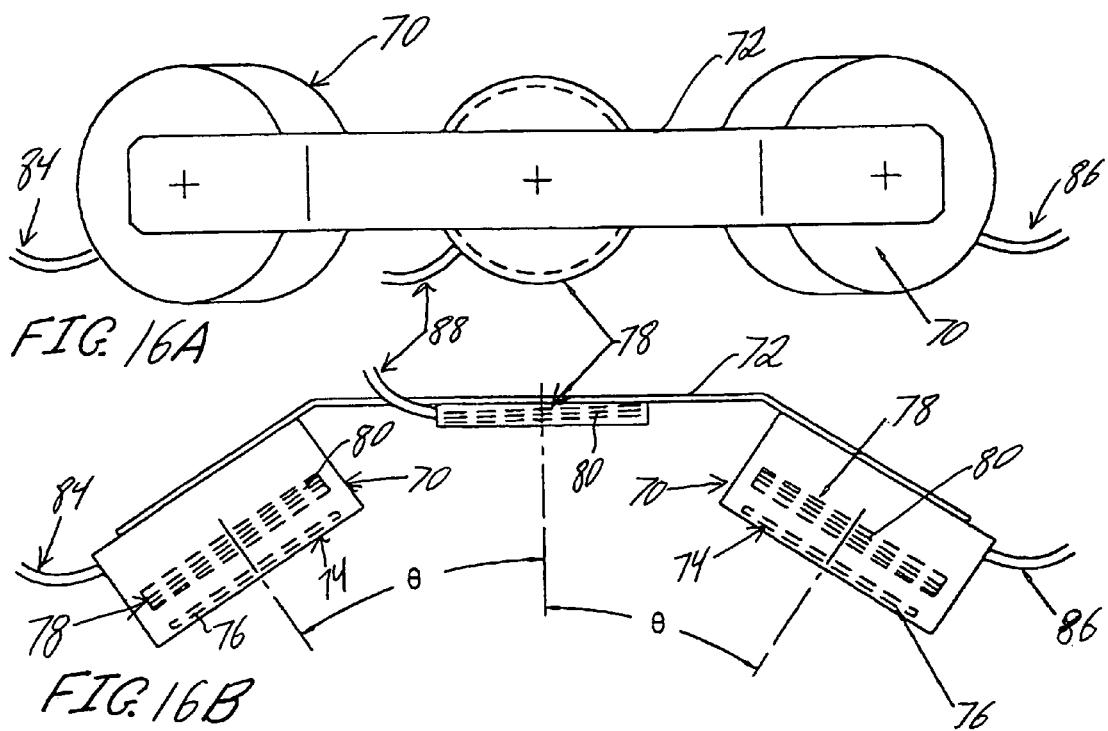

APPARATUS AND METHOD FOR ULTRASONICALLY AND ELECTROMAGNETICALLY TREATING TISSUE

This application claims priority to a U.S. Provisional Application No. 60/135,224 filed on May 21, 1999 by Talish et al., the contents of which are incorporated herein by reference,

BACKGROUND OF THE INVENTION

1. Field of the Invention

The present invention relates to apparatus and method for ultrasonically and electromagnetically stimulating treating tissue, for example, traumatized tissue or a bone injury. More particularly, the present invention relates to apparatus and methods which utilize an ultrasonic transducer assembly in combination with an electromagnetic coil assembly to treat tissue.

2. Description of the Related Art

The use of ultrasound to therapeutically treat and evaluate tissue and bone injuries is known. Impinging ultrasonic pulses having appropriate parameters, e.g., frequency, pulse-repetition, and amplitude, for suitable periods of time and at a proper external location adjacent to a tissue or bone injury has been determined to accelerate the natural healing of, for example, tissue tears, bone breaks and fractures.

U.S. Pat. No. 4,530,360 to Duarte describes a basic non-invasive therapeutic technique and apparatus for applying ultrasonic pulses from an operative surface placed on the skin at a location adjacent a bone injury. To apply the ultrasound pulses during treatment an operator must manually hold the applicator in place until the treatment is complete.

The Duarte patent as well as U.S. Pat. No. 5,520,612 to Winder et al. describe ranges of RF signal for creating the ultrasound, ultrasound power density levels, ranges of duration for each ultrasonic pulse, and ranges of ultrasonic pulse frequencies.

U.S. Pat. No. 5,003,965 to Talish et al. relates to an ultrasonic body treatment system having a body-applicator unit connected to a remote control unit by sheathed fiber optic lines. The signal controlling the duration of ultrasonic pulses and the pulse repetition frequency are generated apart from the body-applicator unit. Talish et al. also describes a mounting fixture for attaching the body-applicator unit to a patient so that the operative surface is adjacent the skin location.

While the systems described in these patents relate to methods and apparatus for ultrasonic diagnosis and/or treatment of hard and soft tissue injuries and defects by applying ultrasound to traumatized tissue, it has been demonstrated that the traumatized tissue heals at a faster rate if the acoustic signal envelope of the applied ultrasonic waves is slowly modulated or perturbed. Modulating the signal envelope of the applied ultrasonic waves can be accomplished by either modulating the envelope of the electrical signal to the ultrasound transducer or by modulating the ultrasonic waves in the body by utilizing-controlled electromagnetic induced forces.

It has also been demonstrated that in the case of a non-union injury, i.e., where a bone fracture fails to heal, that electromagnetic-stimulation (E-stim) treatment of the non-union injury produces a therapeutic response in bone tissue. E-stim generally uses at least an external coil to produce a therapeutic pulsed uniform, electromagnetic field at the fracture site. For example, a pair of Helmholtz coils can produce a constant uniform field at the fracture or wound sites, above the local magnetic field in tissue.

It is generally believed that E-stim promotes and accelerates the healing of non-union injuries due to the creation of a magnetic flux density which causes the creation and movement of ionic charges within the bone tissue. Bone tissue is mainly an ionic-fluid-saturated porous medium having various ions in the intercellular and interstitial fluid such as potassium ions, sodium ions, magnesium ions, chloride ions, phosphate ions, carbonate ions, bicarbonate ions and those formed by the dissociation of amino acids, proteins, sugars, nucleotides and enzymes. The application of a pulsed electromagnetic field, i.e.; the controlled combination of electrostatic and magnetic forces, causes these ions to be charged and moved in a particular direction. The ions diffuse within cells at the treatment area, thereby accelerating the healing process.

According to the present disclosure, the healing of tissue, especially non-union injuries, can be further accelerated by combining ultrasound and E-stim. The forces produced by the applied electromagnetic field add a fluctuating or perturbing force, such as a low frequency modulation force, to the propagating ultrasonic or pressure wave to further stimulate the cells at the treatment area and enhance cellular permeability and ionic diffusion. The largest effect on the acoustic field by the electromagnetic field occurs when the direction of the longitudinal waves is perpendicular to the electromagnetic field, or if the transverse (shear) waves are traveling along the magnetic field lines. The electromagnetic field tends to increase the phase velocity of the ultrasonic waves. The associated magnetic force may be held constant or modulated at a low frequency rate.

SUMMARY OF THE INVENTION

The present invention provides a combined ultrasonic and E-stim treatment apparatus for therapeutically treating traumatic tissue injuries, especially non-union bone fractures, using combined ultrasound and E-stim. The apparatus includes an ergonomically constructed placement module configured for mounting at least one hybrid ultrasonic transducer assembly having an integral signal generator which provides excitation signals to at least one ultrasonic transducer within the placement module for generating an acoustic field. The placement module further includes at least one electromagnetic coil assembly having at least one electromagnetic coil in proximity to each ultrasonic transducer for generating an electromagnetic field. It is contemplated that timing control circuitry as well as monitoring circuitry for the proper control and operation of the components within the placement module are housed within a main operating unit which may be fit within a pouch worn by the patient or integrally contained in the transducer.

In operation, the placement module is positioned adjacent a part of the patient's body such that the at least one ultrasonic transducer is sonically coupled in position adjacent traumatized tissue and/or an osteochondral injury. The at least one ultrasonic transducer and at least one electromagnetic coil are then excited by providing an induced signal to these components. The induced signal causes the at least one ultrasonic transducer to impinge ultrasonic pressure waves against the traumatized tissue and/or injury and for the at least one electromagnetic coil to create an electromagnetic field having a magnetic flux density. The frequency of the induced signal can be varied from 1 Hz to 10,000 Hz. The magnetic flux density adds a fluctuating force to the propagating pressure wave in the body to increase the stimulation of the cells in the vicinity of the injury and to enhance cellular permeability which results in an increase in the diffusion of ions into the cells, such as calcium ions in the case of a non-union bone fracture, resulting in increased protein synthesis. An increase in protein synthesis accelerates bone fracture healing and tissue repair. Additionally, it is contemplated to control the average magnetic flux density, pulse repetition rate, and pulse width of the induced signal for optimal osteogenic stimulation.

Preferably, the main operating unit has an internal power source for powering the signal generator of the ultrasonic transducer assembly, a display for displaying treatment sequence data, a keypad coupled to the signal generator for permitting user operation and/or entry of data. The signal generator includes circuitry having a processor, means for generating a pulsed control signal, and a switch coupled to the processor for regulating the pulsed control signal. The main operating unit further has an alarm for indicating to the user that the treatment time has expired. The alarm is coupled to the processor such that when ultrasonic and E-stim treatment is completed the processor activates the alarm and terminates the induced signal to the components within the placement module.

The present invention also provides a kit for combined ultrasonic and E-stim treatment of traumatized tissue and osteochondrial injuries. The kit includes an ultrasonic transducer assembly having an ultrasonic transducer and signal generator circuitry, an electromagnetic coil assembly having an electromagnetic coil and operating circuitry, a placement module configured for placement therein of the ultrasonic transducer and electromagnetic coil assemblies, and a main operating unit (MOU) or controller coupled to the placement module via a cable. The MOU has an internal power source thereby providing patient mobility. A MOU envisioned for use with the present invention is described in U.S. Pat. No. 5,556,372 to Talish et al. which is hereby incorporated by reference.

The present invention further provides a method for combined ultrasonic and E-stim treatment of traumatized tissue and/or osteochondrial injuries. The method entails the steps of locating the site of the injury; positioning a placement module containing at least one ultrasonic transducer assembly and at least one electromagnetic coil assembly adjacent to the injury such that the at least one ultrasonic transducer and at least one electromagnetic coil of the at least one ultrasonic transducer and at least one electromagnetic coil assemblies, respectively, are in proximity to the injury; activating the at least one ultrasonic transducer and the at least one electromagnetic coil for simultaneously propagating at least one ultrasonic pressure wave towards the injury and creating an electromagnetic field for adding a fluctuating force to the propagating pressure wave.

In an alternative embodiment, a placement module is provided for securing a plurality of ultrasonic transducers and a plurality of electromagnetic coils thereto in a plurality of configurations. The placement module is then secured in proximity to traumatized tissue and/or an osteochondrial injury to provide ultrasonic and E-stim treatment.

BRIEF DESCRIPTION OF THE DRAWINGS

Preferred embodiments of the invention are described below with reference to the drawings, which are described as follows:

FIG. 2 is a perspective view of an insert secured in a cast ready to receive a combined ultrasound and E-stim transducer head of a portable ultrasonic and E-stim treatment apparatus of a first embodiment;

FIG. 3 is a perspective view of the transducer head of FIG. 2 fully mounted to the cast;

FIG. 5A is a top view of the placement module of FIG. 2 illustrating the size and position of an ultrasonic transducer in relation to the size and position of an electromagnetic coil within the placement module;

FIG. 5B is a cross-sectional view of the placement module of FIG. 2;

FIG. 6A is a top view of a placement module of a portable ultrasonic and E-stim treatment apparatus of another embodiment illustrating the size and position of an ultrasonic transducer in relation to the size and position of an electromagnetic coil within the placement module;

FIG. 6B is a cross-sectional view of the placement module of FIG. 6A;

FIG. 7A is a top phantom view of a placement module of a portable ultrasonic and E-stim treatment apparatus of another embodiment illustrating the size and position of an ultrasonic transducer in relation to the size and position of an electromagnetic coil within the placement module;

FIG. 7B is a cross-sectional view of the placement module of FIG. 7A;

FIG. 8 is a cross-sectional view of a placement module of a portable ultrasonic and E-stim treatment apparatus of another embodiment illustrating the position of an ultrasonic transducer in relation to the position of a cross-shaped electromagnetic coil within the placement module;

FIG. 9 is a cross-sectional view of a placement module of a portable ultrasonic and E-stim treatment apparatus of another embodiment illustrating the position of an ultrasonic transducer in relation to the position of a cross-shaped electromagnetic coil within the placement module;

FIG. 10 is a cross-sectional view of a placement module of a portable ultrasonic and E-stim treatment apparatus of another embodiment illustrating the position of an ultrasonic transducer in relation to the position of a star-shaped electromagnetic coil within the placement module;

FIG. 11A is a top view of a placement module of a portable ultrasonic and E-stim treatment apparatus of another embodiment illustrating the size and position of an ultrasonic transducer in relation to the size and position of an electromagnetic coil within the placement module;

FIG. 11B is a cross-sectional view of the placement module of FIG. 11A;

FIG. 12A is a top view of a placement module of a portable ultrasonic and E-stim treatment apparatus of a further embodiment illustrating the size and position of an ultrasonic transducer in relation to the size and position of an electromagnetic coil within the placement module;

FIG. 12B is a cross-sectional view of the placement module of FIG. 12A;

FIG. 13A is a top phantom view of a placement module of a portable ultrasonic and E-stim treatment apparatus of another embodiment illustrating the size and position of an ultrasonic transducer in relation to the size and position of an electromagnetic coil within the placement module;

FIG. 13B is a first cross-sectional view of the placement module of FIG. 13A;

FIG. 13C is a second cross-sectional view of the placement module of FIG. 13A;

FIG. 14A is a top view of a placement module of a portable ultrasonic and E-stim treatment apparatus of another embodiment illustrating the size and position of an ultrasonic transducer in relation to the size and position of an electromagnetic coil within the placement module;

FIG. 14B is a cross-sectional view of the placement module of FIG. 14A;

FIG. 15A is a top view of a placement module of a portable ultrasonic and E-stim treatment apparatus of yet another embodiment illustrating the size and position of an ultrasonic transducer in relation to the size and position of an electromagnetic coil within the placement module;

FIG. 15B is a cross-sectional view of the placement module of FIG. 15A;

FIG. 16A is a top view of a placement module of a portable ultrasonic and E-stim treatment apparatus of another embodiment having a plurality of ultrasonic transducers and a plurality of electromagnetic coils; and FIG. 16B is a cross-sectional view of the placement module of FIG. 16A.

DETAILED DESCRIPTION OF THE PREFERRED EMBODIMENTS

Figure 1:
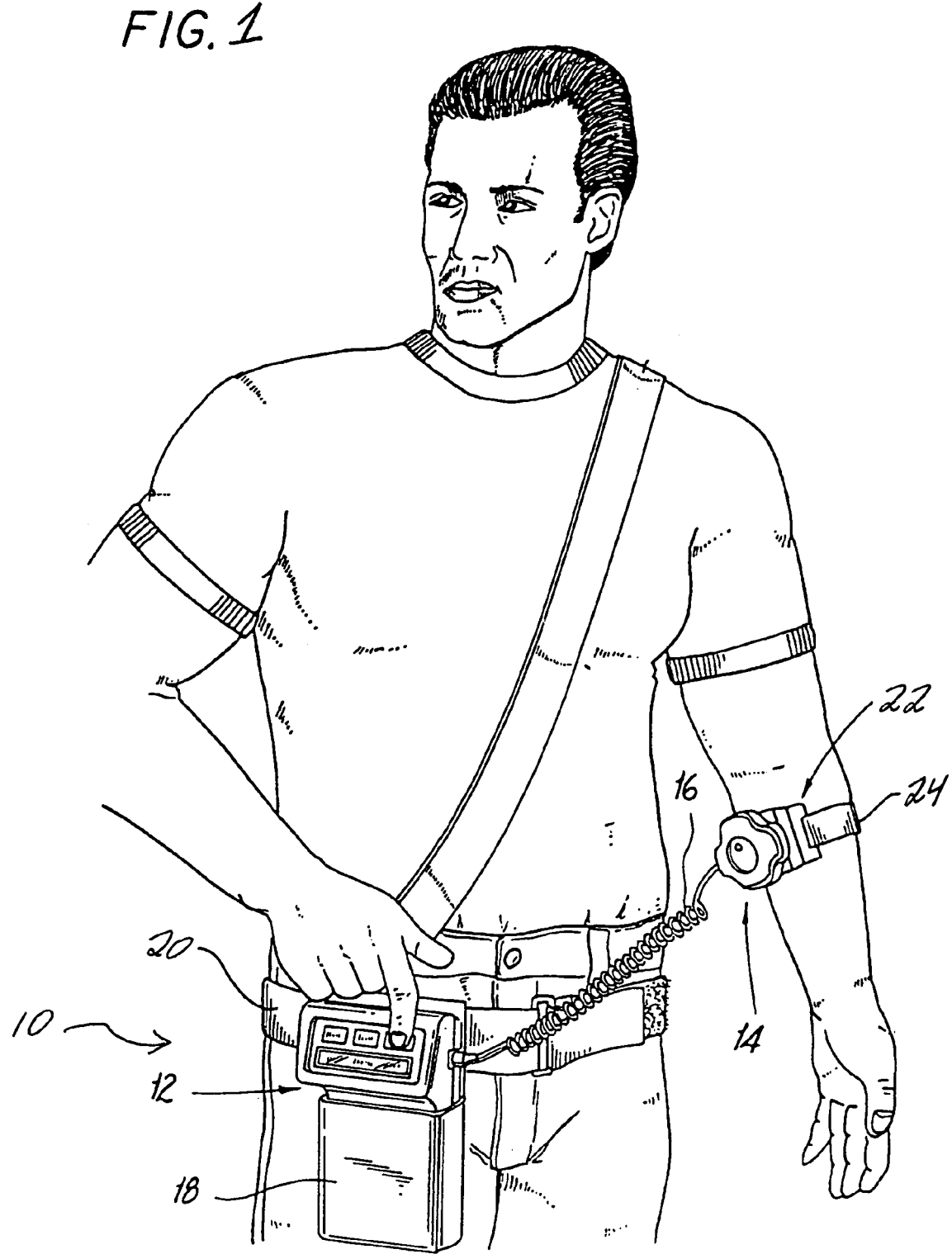
FIG. 1 is a perspective view of a patient wearing a portable ultrasonic and E-stim treatment apparatus of a first embodiment according to the present invention having a main operating unit or controller and a placement module.

Preferred embodiments of the present invention will be described in detail with reference to the attached drawings. Like reference numerals denote the same or similar components in the drawings.

The ultrasonic and E-stim treatment apparatus and methods of the present invention are used for the surgically non-invasive application of ultra high-frequency acoustic energy and magnetic flux density in the treatment of traumatized tissue and/or osteochondrial injuries. Even though this detailed description discusses the treatment of traumatized tissue and/or osteochondrial injuries, the ultrasound and E-stim treatment apparatus can be used to treat osteochondrial defects caused by e.g., medication, infection or metabolic processes.

A. Background Information Relating to the Embodiments Described Herein

1. Pulsed Low Intensity Ultrasound Excitation

Ultrasound wave propagation in tissue exerts a unidirectional radiation force on all absorbing and reflecting obstacles in its path, even at the microstructural level. Low-intensity ultrasound refers to those power levels that just exceed biological thresholds which trigger or evoke general biological regulatory reactions. Although too low to produce direct measurable biological effects, clinical results have established that low intensity ultrasound is sufficient to invoke biological healing processes.

Since the early sixties, the specific physical and biological mechanisms behind the thereapeutic effectiveness of low intensity ultrasound have been extensively investigated. For spatial average-temporal average (SATA) intensities from 0.1–0.5 W/cm$^2$, it is possible to produce the non-thermal, high stress mechanisms of acoustic streaming and cavitation. In vitro tests on isolated fibroblast cells have shown that the effects of ultrasound on the cells are pressure sensitive, suggesting a stable cavitation mechanism. The resulting bubble oscillations, possibly including acoustic microstreaming, can generate high shear stress on the cell membrane, which can affect the cell's permeability to sodium and calcium ions. The increase in cell permeability may result in an increase in calcium uptake, and increase in protein and DNA synthesis in fibroblasts, and account for the observed activation of macrophages. The production of fibroblasts and macrophages characterizes the normal fracture repair process.

For SATA intensities below 0.1 W/cm$^2$, stable cavitation and acoustic micro-streaming seem quite unlikely. In vivo test results indicate that a low SATA intensity from 30–50 mW/cm$^2$ is highly effective in stimulation bone fracture repair. These results support the thesis that ultrasonically-induced mechanical vibrations tend to increase the permeability of the cell membrane to calcium ions. Preliminary clinical results indicate that the initial result of applying pulsed, low intensity ultrasound to traumatized tissue is to increase blood flow in the local region. It is proposed that the increased vascularity and the micromechanical fluid pressure appears to produce an increase in cellular calcium uptake, resulting in increased protein synthesis, thereby accelerating bone fracture healing and tissue repair.

2. Significance of Ultrasound Modulation to Stimulate Vascularity

Test results have shown that there is an increase in vascularity produced with the application of ultrasound to traumatized tissue. In treating bone fractures, the increase in blood flow to the callus, for example, may prove significant in accelerating bone healing. The test results referred to were obtained with an acoustic longitudinal wave and a constant (0 Hz) modulation envelope. It was clearly established that bone healing initially occurs in the periosteal region, followed by healing within the fracture itself (endosteal healing). The increased vascular flow due to ultrasound stimulation occurred in the region of the periosteum. It is proposed that the acoustic wave stimulates the exposed nerve endings of the periosteum, thereby stimulating local vascularization. The acoustic wave is preferably a constant envelope sine wave at a carrier frequency of 1.5 MHZ and a repetition frequency of 1.0 kHz.

A slowly modulated acoustic signal envelope, at a rate less than 100 Hz, may prove to be more osteogenic, both in the fracture gap and on the periosteum. It has been demonstrated that the micromechanical stimuli (0.5 Hz for 17 minutes, daily) significantly improves the healing of tibial fractures. This accelerated healing process has been correlated with the promotion of fracture revascularization. The modulation of the excitation may be accomplished by either modulating the envelope of the electrical signal to the ultrasound transducer or by modulating the pressure wave in the body, utilizing controlled electromagnetic induced forces.

3. Low-Frequency Electromagnetic Excitation

In cases where the fracture fails to heal, referred to as a non-union, the most common treatment is surgery or electro-magnetic-stimulation (E-stim). As discussed above, E-stim uses an external coil to produce a therapeutic pulsed electromagnetic field at the fracture site.

4. Combined Ultrasonic and Electromagnetic Stimulation

Specifically, the combined ultrasonic and E-stim treatment methods and apparatus of the present invention generate and control the spatial distribution of a non-uniform, time-varying, directionally-oriented electromagnetic field to produce an ionic current and electric voltage, relative to the spatial and temporal generation and control of a time-varying, directionally-oriented non-uniform acoustic pressure wave, in living tissue. The main physical factors that characterize ultrasound propagation in tissue are mechanical, affecting the particle displacement, velocity, acceleration, and pressure at the microstructural level.

In preferred embodiments of the present invention, the forces produced by the applied electromagnetic field are employed to add a perturbing or fluctuating force, such as a low frequency modulation force, to the propagating pressure wave in the body to increase the stimulation of the cells in the vicinity of the injury and to enhance cellular permeability which results in an increase in the diffusion of ions into the cells, such as calcium ions in the case of a non-union bone fracture, resulting in increased protein synthesis. As indicated above, an increase in protein synthesis accelerates bone fracture healing and tissue repair.

The low frequency perturbation of the propagating pressure wave can be produced by positioning the electromagnetic coil in a wide variety of orientations relative to the direction of the propagating pressure wave. The largest effect on the pressure wave occurs when the direction of the longitudinal pressure wave is perpendicular to the magnetic field, or if the transverse (shear) waves are traveling along the magnetic field lines. In this case, the magnetic field tends to increase the phase velocity of the sound wave. The associated magnetic force may be held constant or modulated at a low frequency rate by controlling the magnitude of an induced signal to the electromagnetic coil.

Consider the effect of a magnetic field on the propagation of a sound wave in a conducting fluid, such as the soft tissue-bone complex. Bone tissue is mainly an ionic-fluid-saturated porous medium having various ions in the intercellular and interstitial fluid, such as potassium ions, sodium ions, magnesium ions, chloride ions, phosphate ions, carbonate ions, bicarbonate ions and those formed by the dissociation of amino acids, proteins, sugars, nucleotides and enzymes. The movement of charged ions by the controlled combination of electrostatic, magnetic and acoustic radiation forces can promote and accelerate tissue healing. The interrelationships between these physical entities can be depicted by the general acoustic wave equation in a solid, homogeneous medium.

It is well known that the magnetic force F on a positive charge q moving with a velocity v in a magnetic field of flux density B is given by the vector product $F=qv \times B$. The vector product gives the same direction for F as does the classic Fleming's left-hand rule and establishes that F is perpendicular to B. If the longitudinal acoustic waves are propagated in the direction of the magnetic flux, there is no effect on the acoustic field. As indicated above, the largest effect to the acoustic field occurs when the direction of the longitudinal waves is perpendicular to the magnetic field, or if the transverse (shear) waves are traveling along the magnetic field lines.

In general, the acoustic waves can travel at an arbitrary angle with respect to the magnetic field flux lines. When this occurs, the nature of the resulting acoustic wave will depend markedly on whether the fluid velocity is parallel with or perpendicular to the plane established by k (wavenumber) and B. If the particle velocity is perpendicular to the k-B plane, then the wave motion will be transverse, having a velocity equal to $B \cos \theta / \sqrt{\rho}$, where $\theta$ is the angle between the direction of propagation and the magnetic field, and $\rho$ is the fluid density. If the particle velocity vector lies in the k-B plane, then the wave mode will contain both a transverse and a longitudinal wave, corresponding to the particle velocity components perpendicular and parallel with k, respectively. It is shown that a density fluctuation is produced only if there is a velocity component in the direction of propagation and the perturbation in the magnetic field is always perpendicular to k.

B. Embodiments of the Present Invention

The various embodiments of the present invention include an ergonomically constructed placement module having a strap or other fastening means for being secured adjacent an injured part of a patient's body. At least one ultrasonic transducer assembly and at least one electromagnetic coil assembly are attached to or housed within the placement module and properly positioned in proximity to the traumatized tissue and/or osteochondrial injury. The at least one ultrasonic transducer assembly includes at least one ultrasonic transducer and the at least one electromagnetic coil assembly includes at least one electromagnetic coil. Different types of ultrasonic transducers and signals can be provided, such as those described and schematically depicted in U.S. Pat. No. 5,520,612 to Winder et al. which is hereby incorporated by reference. Additionally, ultrasonic transducers can be used such as those described and illustrated in U.S. patent application Ser. No. 09/040,155 filed on Mar. 17, 1998, the contents of which are incorporated herein by reference.

The apparatus preferably uses electromagnetic field coil configurations to produce asymmetric, non-uniform or time-varying fields which can be used for selective spatial stimulation in tissue. In the embodiments described below the frequency of the induced signal to the at least one ultrasonic transducer and at least one electromagnetic coil can be varied from 1 Hz to 10 KHz. It is preferred that for optimal osteogenic stimulation, in the treatment of non-union bone fractures, that the average magnetic flux density, pulse repetition rate, and pulse width of the induced signal be controlled. Precise control of the average magnetic flux implies considering the combined magnetic field of the applied magnetic field via the at least one electromagnetic coil and the local magnetic fields. The latter includes the Earth's magnetic field and the effects of ferromagnetic materials in the vicinity which create additional magnetic flux that flows through tissue.

The apparatus also preferably utilizes a portable, ergonomically constructed main operating unit (MOU) having an internal power source which is worn by the patient. The internal power source provides control signals to the ultrasonic transducers and electromagnetic coils at the placement module. It is preferred that the electromagnetic coils produce time-varying, non-uniform electromagnetic fields. The MOU which is utilized is preferably the one described in U.S. Pat. No. 5,556,372 to Talish et al.; the contents of which are incorporated herein by reference. The ultrasonic transducers and associated circuitry preferably used are described in U.S. application Ser. No. 09/040,157; the contents of which are incorporated-herein by reference.

Turning to the figures, in particular FIG. 1, a patient wearing a first embodiment of the portable ultrasonic and E-stim treatment apparatus of the present invention is shown. The ultrasonic and E-stim treatment apparatus designated generally by reference numeral 10 includes a MOU 12, a placement module 14, and a cable 16 connecting the MOU 12 with the placement module 14. The MOU 12 is positioned within a pouch or carrying case 18 which is strapped to the patient by a harness 20 to provide mobility to the patient during treatment. The placement module 14 is secured to a mounting assembly 22 having a placement band 24 for placing and securing the placement module 14 in proximity to a treatment area. The placement band 24 is configured to firmly secure the placement module 14 to the patient. A sponge-like material may preferably line the inner surface of the placement band 24 for providing comfort to the patient and to prevent window edema.

Referring to FIGS. 2 and 3, another embodiment of the portable ultrasonic and E-stim treatment apparatus of the present invention is shown. An insert 90 is shown secured within a cast 92 of a patient requiring ultrasound treatment. A tab 94 which is attached at its lower end to a transmissionenhancing medium is shown extending from insert 90. Following the placement of ultrasound transducer head module 96 into insert 90, a cover 98 is placed over the top of the insert 90 and strap 100 is adjusted to secure the entire apparatus in place. The ultrasound transducer head module 96 is similar to the placement module 14 shown in FIG. 1. The ultrasound transducer array can transmit signals designed for therapeutic and/or diagnostic operation. In the diagnostic mode, reflection echo data is processed upon reception for imaging and tissue analysis. As used herein, one means for receiving reflected diagnostic data includes the VS transducer assembly, used circuitry or software in the MOU for processing and/or analyzing the echo returns.

Figure 4:
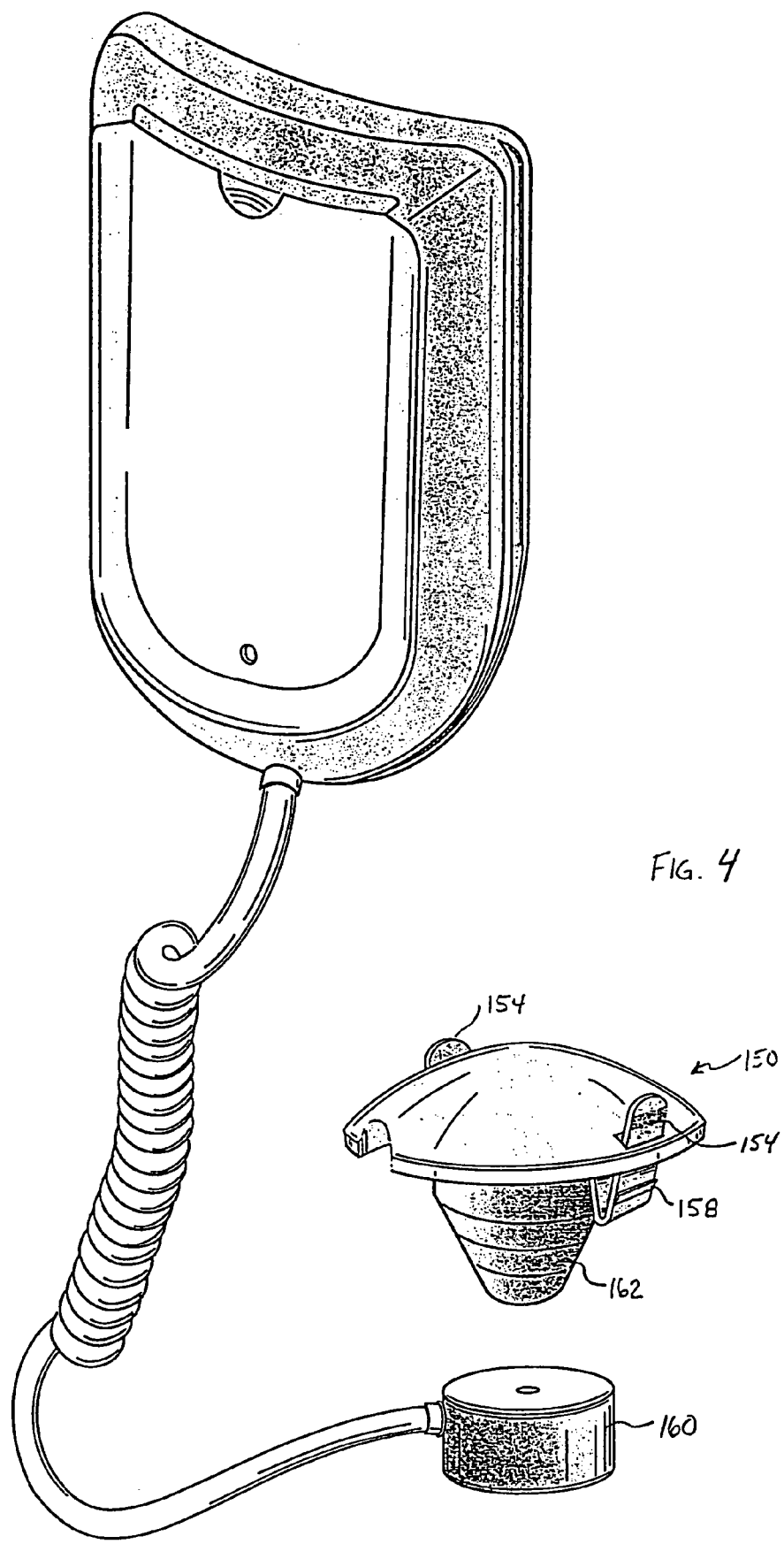
FIG. 4 is a perspective view of another embodiment of a combined ultrasound and E-stim transducer head having a cover with locking structure.

With reference to FIG. 4, another embodiment of the ultrasound and E-stim treatment apparatus is shown. FIG. 4 illustrates a perspective view of a cover 150 having locking structure. The cover 150 has two locking tabs 154 for locking the cover within an insert. A protrusion 158 is similarly formed on locking tab 154 to engage a groove on the inner surface of an insert. Also shown in FIG. 4 is an ultrasound treatment module with treatment head 160 which is similar to the placement module 14 shown in FIG. 1. Furthermore, a conical helical spring 162 is connected to a lower surface of the cover 150 to bias the treatment head 160 in a direction toward a treatment site.

With reference to FIGS. 5A to 7B, there are shown top and cross-sectional views of the placement module 14 of the embodiments of FIG. 2 (FIGS. 5A and 5B), FIGS. 6A and 6B, and FIGS. 7A and 7B. These embodiments each have an ultrasonic transducer assembly 26 and an electromagnetic coil assembly 28. The ultrasonic transducer assembly 26 includes at least one ultrasonic transducer 30 and related circuitry, including a signal generator (not shown). The electromagnetic coil assembly 28 includes at least one electromagnetic coil 32. The ultrasonic transducer 30 and the electromagnetic coil 32 are positioned differently with respect to each other for each of these embodiments, as described herein below. Further, in these embodiments, the ultrasonic transducer 30 is positioned below the electromagnetic coil 32, i.e., closer to the injury, and has a smaller diameter than the electromagnetic coil 32.

The ultrasonic transducer assembly 26 and electromagnetic coil assembly 28 for these embodiments are coupled to the MOU 12 by cable 16. The cable 16 is preferably a multi-conductor cable capable of transmitting relatively low frequency RF or optical signals, as well as digital signals. The cable 16 may include coaxial cable or other types of suitable shielded cable. Alternatively, the cable 16 may include fiber optic cable for transmitting optical signals.

The signals from the MOU 12 may be transmitted continuously or as a series of pulses. It is contemplated that a voltage magnitude of the signals to the ultrasonic transducer 30 be varied to vary a transmission power of the propagated ultrasonic waves. Further, it is contemplated that a voltage magnitude of the signal to the electromagnetic coil 32 be varied to vary the magnetic flux density.

With reference to FIGS. 5A and 5B, the electromagnetic coil 32 is positioned parallel to the ultrasonic transducer 30. In this configuration, the longitudinal acoustic waves are propagated in the same direction as the magnetic flux, and hence this configuration provides the smallest effect on the acoustic field. For example, since the electromagnetic coil 32 is parallel to the horizontal axis, when a current is supplied to the electromagnetic coil 32, the resulting magnetic flux is parallel to the longitudinal axis of the electromagnetic coil 32 according to Maxwell's Equations. Hence, the magnetic flux is in the same direction as the propagating longitudinal acoustic waves.

In FIGS. 6A and 6B, the electromagnetic coil 32 is positioned at an angle θ with respect to the horizontal axis of the placement module 14. In this configuration, the longitudinal acoustic waves are propagated at the same angle θ with respect to the direction of the magnetic flux, and hence this configuration provides a noticeable effect on the acoustic field.

In FIGS. 7A and 7B, the electromagnetic coil 32 is positioned transverse to the ultrasonic transducer 30. In this configuration, the longitudinal acoustic waves are propagated transverse to the direction of the magnetic flux, and hence this configuration provides the largest effect on the acoustic field.

With reference to FIGS. 8 to 10, there are shown cross-sectional views of further embodiments of the present invention. These embodiments each have an ultrasonic transducer assembly 36 and an electromagnetic coil assembly 38 housed within a placement module 40. The ultrasonic transducer assembly 36 includes an ultrasonic transducer 42 and related circuitry, including a signal generator (not shown). The electromagnetic coil assembly 38 includes a cross-shaped electromagnetic coil 44 or star-shaped electromagnetic coil 46: The ultrasonic transducer 42 and the electromagnetic coils 44 and 46 are positioned differently with respect to each other for each of these embodiments, as described herein below. Further, in these embodiments, the ultrasonic transducer 42 is positioned below the electromagnetic coils 44 and 46, i.e., closer to the injury, and has a larger diameter than the electromagnetic coils 44 and 46. Cross-shaped electromagnetic coil 44 has a first coil 48 and a second coil 50. Star-shaped electromagnetic coil 46 has a first coil 52, a second coil 54, and a third coil 56.

The ultrasonic transducer assembly 36 and electromagnetic coil assembly 38 are coupled to a MOU (not shown) similar to MOU 12 shown in FIG. 1 or MOU 110 shown in FIG. 2 by cable 16. Signals transmitted via the cable 16 to the components within placement module 40 may be transmitted continuously or as a series of pulses.

With reference to FIG. 8, the first and second coils 48 and 50 of the cross-shaped electromagnetic coil 44 are perpendicular to each other and positioned at an acute angle θ with respect to a longitudinal axis of the placement module 40. In this configuration, a magnetic flux is created transverse to first coil 48 and another magnetic flux is created transverse to second coil 50. Since both coils 48 and 50 are perpendicular to each other and at an angle θ with respect to the longitudinal axis of the placement module 40, the longitudinal acoustic waves propagated by the ultrasonic transducer 42 are modulated or perturbed by a first magnetic flux created by the first coil 48 and a second magnetic flux created by the second coil 50. It is believed that modulation of the acoustic waves by the first and second magnetic fluxes stimulates and enhances cellular permeability and the diffusion of ions within the traumatized tissue or osteochondrial injury to accelerate healing thereof as discussed above.

In FIG. 9, the first and second coils 48 and 50 of the cross-shaped electromagnetic coil 44 are perpendicular to each other, but positioned at a right angle θ with respect to a longitudinal axis of the placement module 40. In this configuration, a magnetic flux is created transverse to first coil 48 and another magnetic flux is created transverse to second coil 50. Since both coils 48 and 50 are perpendicular to each other and at a right angle θ with respect to the longitudinal axis of the placement module 40, the longitudinal acoustic waves propagated by the ultrasonic transducer 42 are greatly modulated or perturbed by a first magnetic flux created by the first coil 48 and slightly modulated by a second magnetic flux created by the second coil 50. Accordingly, by changing the position of the electromagnetic coil assembly 44 within the placement module 40, the amount of modulation of the acoustic waves can be controlled for optimal osteogenic stimulation. It is contemplated to provide different circuitry for driving the first coil 48 and the second coil 50 to alternate between the creation of the first magnetic flux and the second magnetic flux during ultrasonic and E-stim treatment using the apparatus.

As shown in FIG. 10, the first, second and third coils 52, 54 and 56 of the star-shaped electromagnetic coil 46 are positioned at an acute angle θ with respect to each other and at the same angle θ with respect to a longitudinal axis of the placement module 40 if one of the coils 52, 54 and 56 is perpendicular to the longitudinal axis. In this configuration, a first magnetic flux is created transverse to the first coil 52, a second magnetic flux is created transverse to the second coil 54, and a third magnetic flux is created transverse to the third coil 56. By controlling the orientation of the three coils 52, 54 and 56, the direction of the first, second and third magnetic fluxes can be controlled to vary the amount of modulation of the acoustic waves propagated by the ultrasonic transducer 42.

With reference to FIGS. 11A to 15B, there are shown various top and cross-sectional views of variations of placement module 60. All of these variations have an ultrasonic transducer assembly 26 and an electromagnetic coil assembly 28. The ultrasonic transducer assembly 26 includes an ultrasonic transducer 30 and related circuitry, including a signal generator (not shown). The electromagnetic coil assembly 28 includes an electromagnetic coil 32. The ultrasonic transducer 30 and the electromagnetic coil 32 are positioned differently with respect to each other for each of the variations illustrated by FIGS. 11A to 15B, as described herein below. Further, in the variations illustrated by FIGS. 11A to 15B, the ultrasonic transducer 30 is positioned below the electromagnetic coil 32, i.e., closer to the injury.

The electromagnetic coil assembly 28 and the ultrasonic transducer assembly 26 are individually coupled by cables 62 and 64, respectively, to a MOU (not shown). The MOU can be similar to MOU 12 of the embodiment shown in FIG. 1 or MOU 110 of the embodiment shown in FIG. 2. The cables 62 and 64 are preferably multiconductor cables capable of transmitting relatively low frequency RF or optical signals, as well as digital signals. The cables 62 and 64 may include coaxial cable or other types of suitable shielded cable. Alternatively, the cables 62 and 64 may include fiber optic cable for transmitting optical signals. The signals may be transmitted continuously or as a series of pulses. Additionally, with respect to these embodiments, the signals may be transmitted at different times and at varying periods for driving the ultrasonic transducer and electromagnetic coil assemblies at different times with respect to each other, since the assemblies are not powered by the same cable as in other embodiments.

With reference to FIGS. 11A and 11B, the electromagnetic coil 32 is positioned in a housing 66 which is positioned on top of the placement module 60. The electromagnetic coil 32 is parallel to the ultrasonic transducer 30 within the placement module 60. In this configuration, the longitudinal acoustic waves are propagated in the same direction as the magnetic flux, and hence this configuration provides the smallest effect on the acoustic field. For example, since the electromagnetic coil 32 is parallel to the horizontal axis, when a current is supplied to the electromagnetic coil 32, the resulting magnetic flux is parallel to the longitudinal axis of the electromagnetic coil 32 according to Maxwell's Equations. Hence, the magnetic flux is in the same direction as the propagating longitudinal acoustic waves.

In FIGS. 12A and 12B, the electromagnetic coil 32 is positioned within the housing 66 and at an angle θ with respect to the horizontal axis of the placement module 60. In this configuration, the longitudinal acoustic waves are propagated at the same angle θ with respect to the direction of the magnetic flux, and hence this configuration provides a noticeable effect on the acoustic field.

In FIGS. 13A to 13C, the electromagnetic coil 32 is positioned within the housing 66 and transverse to the ultrasonic transducer 30. In this configuration, the longitudinal acoustic waves are propagated transverse to the direction of the magnetic flux, and hence this configuration provides the largest effect on the acoustic field.

FIGS. 14A and 14B show the electromagnetic coil 32 wrapped around the placement module 60. The electromagnetic coil 32 is wrapped parallel to the ultrasonic transducer 30 within the placement module 60. In this configuration, the longitudinal acoustic waves are propagated in the same direction as the magnetic flux, and hence this configuration provides the smallest effect on the acoustic field. For example, since the electromagnetic coil 32 is parallel to the horizontal-axis, when a current is supplied to the electromagnetic coil 32, the resulting magnetic flux is parallel to the longitudinal axis of the electromagnetic coil 32 according to Maxwell's Equations. Hence, the magnetic flux is in the same direction as the propagating longitudinal acoustic waves.

In FIGS. 15A and 15B, the electromagnetic coil 32 is wrapped around the housing 66 at an angle θ with respect to the horizontal axis of the placement module 60. In this configuration, the longitudinal acoustic waves are propagated at the same angle θ with respect to the direction of the magnetic flux, and hence this configuration provides a noticeable effect on the acoustic field.

FIGS. 16A and 16B show two placement modules 70, similar to placement module 14 of FIG. 2, attached to a placement band 72. The placement modules 70 each house an ultrasonic transducer assembly 74 having an ultrasonic transducer 76 and an electromagnetic coil assembly 78 having an electromagnetic coil 80. An additional electromagnetic coil assembly 78 is positioned between the two placement modules 70. This arrangement is particularly advantageous in spinal repair and intervertebral fusion procedures wherein ultrasound and electromagnetic energy is focused at the site. The two placement modules 70 and the additional electromagnetic coil assembly 82 are positioned at an angle θ with respect to each other and are powered by respective cables 84, 86 and 88, respectively, connected to an MOU (not shown) similar to MOU 12 or MOU 110. It is contemplated that the placement band 72 be manufactured from a flexible material to enable the placement band 72 to be positioned in a plurality of configurations.

In operation the placement band 72 is affixed in proximity to the traumatized tissue or osteochondral injury. The ultrasonic transducers 76 and the electromagnetic coils 80 are then activated for a predetermined amount of time to impinge modulated acoustic waves at the injury site. It is contemplated that the electromagnetic coils 80 can be positioned in a variety of positions to control the amount of modulation as discussed above with reference to several embodiments. It is further contemplated to individually drive the ultrasonic transducers 76 and the electromagnetic coils 80 at different times and at varying periods.

It is additionally contemplated to construct the placement band 72 from suitable conductive plastics, such as conductive ABS plastics with either carbon, stainless steel, nickel or aluminum fibers to forego the use of wires for connecting each ultrasonic transducer and electromagnetic coil assembly to a specific cable. In such an embodiment, the conductive placement band would be used to electrically connect the ultrasonic transducer: and electromagnetic coil assemblies to an MOU via a single cable.

It is also contemplated to provide each of the embodiments of the present invention as a kit for combined ultrasonic and E-stim treatment of traumatized tissue and osteochondrial injuries. The kit can include the ultrasonic transducer assembly having the ultrasonic transducer and signal generator circuitry, the electromagnetic coil assembly having the electromagnetic coil and operating circuitry, the placement module configured for placement therein of the ultrasonic transducer and electromagnetic coil assemblies, and the main operating unit (MOU) coupled to the placement module.

For all the embodiments disclosed herein, it is contemplated that an ultrasound conducting gel be positioned between the placement modules of the embodiments herein and the injured part of the patient's body to prevent attenuation of the ultrasonic waves. It is also contemplated that one or more transducers can be converted to receive reflected diagnostic data from the treatment site. This permits real time evaluation of the injury site and healing process.

Block diagrams of first and second preferred embodiments of the ultrasonic transducer assembly circuitry is shown by FIGS. 6 and 6A in U.S. Pat. No. 5,556,372, the contents of which are incorporated herein by reference.

It will be understood that various modifications can be made to the various embodiments of the present invention herein disclosed without departing from its spirit and scope. For example, various modifications may be made in the structural configuration of the placement modules and the configuration of the ultrasonic transducer and electromagnetic coil assemblies. Therefore, the above description should not be construed as limiting the invention but merely as presenting preferred embodiments of the invention. Those skilled in the art will envision other modifications within the scope and spirit of the present invention as defined by the claims presented below.

What is claimed is:

1. A treatment assembly for providing ultrasonic and electromagnetic stimulation to a treatment area adjacent to a bone defect or injury, said assembly comprising:
   at least one ultrasonic transducer assembly having at least one ultrasonic transducer;
   at least one electromagnetic coil assembly having at least one electromagnetic coil operatively associated with said at least one ultrasonic transducer assembly;
   a placement module configured to be worn by a patient, said placement module being configured to receive said at least one ultrasonic transducer assembly and said at least one electromagnetic coil assembly such that when said placement module is worn said at least one ultrasonic transducer and said at least one electromagnetic coil are positioned to provide modulated ultrasound energy and electromagnetic energy towards said treatment area adjacent to the bone defect or injury, wherein the at least one electromagnetic coil is adapted to be selectively positioned in different orientations with respect to the ultrasonic transducer to vary the modulation of the ultrasound energy towards said treatment area adjacent to said bone defect or injury; and
   a main operating unit for providing at least one driving signal to said at least one ultrasonic transducer assembly for driving said at least one ultrasonic transducer and said at least one electromagnetic coil to provide ultrasonic and electromagnetic stimulation to said treatment area adjacent to the bone defect or injury.

2. The treatment assembly according to claim 1, wherein said main operating unit is coupled to said at least one ultrasonic transducer assembly by a first cable and said at least one electromagnetic coil assembly by a second cable for providing said at least one driving signal to the at least one ultrasonic transducer assembly and said at least one electromagnetic coil assembly at different times and at varying periods.

3. The treatment assembly according to claim 2, wherein said at least one ultrasonic transducer is positioned closer to said treatment area than said at least one electromagnetic coil when said placement module is positioned in proximity to said treatment area adjacent to the bone defect or injury.

4. The treatment assembly according to claim 1, wherein said at least one electromagnetic coil is positioned at an angle θ with respect to a horizontal axis of said at least one ultrasonic transducer, wherein θ is greater than or equal to zero degrees and less than or equal to 90 degrees.

5. The treatment assembly according to claim 1, wherein said at least one electromagnetic coil is wrapped around said placement module.

6. The treatment assembly according to claim 1, wherein said placement module is constructed from a conductive material and said at least one ultrasonic transducer and said at least one electromagnetic coil are electrically coupled to said main operating unit via said conductive material.

7. The treatment assembly according to claim 1, wherein said at least one ultrasonic transducer includes means for receiving reflected diagnostic data.

8. The treatment assembly according to claim 1, wherein said at least one electromagnetic coil provides a non-uniform electromagnetic field.

9. A method for ultrasonically and electromagnetically treating tissue and bone defect or injuries, said method comprising:
   providing a main operating unit having an internal power source coupled to at least one ultrasonic transducer assembly and at least one electromagnetic coil assembly, said at least one ultrasonic transducer assembly includes at least one ultrasonic transducer, said at least one electromagnetic coil assembly includes at least one electromagnetic coil;
   providing a placement module configured to receive said at least one ultrasonic transducer assembly and said at least one electromagnetic coil assembly such that when said placement module is secured to a patient's body said at least one ultrasonic transducer and said at least one electromagnetic coil are positioned to provide modulated ultrasound energy and electromagnetic energy towards a treatment area adjacent to a bone defect or injury, wherein the at least one electromagnetic coil is adapted to be selectively positioned in different orientations with respect to the ultrasonic transducer to vary the modulation of the ultrasound energy towards said treatment area adjacent to said bone defect or injury;
   exciting said at least one ultrasonic transducer to impinge ultrasonic waves towards the treatment area adjacent to the bone defect or injury; and
   exciting said at least one electromagnetic coil to create an electromagnetic field.

10. The method according to claim 9, wherein said steps of exciting said at least one ultrasonic transducer and said at least one electromagnetic coil are performed simultaneously by transmitting a control signal from said main operating unit.

11. The method according to claim 9, wherein said steps of exciting said at least one ultrasonic transducer and said at least one electromagnetic coil are performed independently by transmitting from said main operating unit at least a first control signal to excite said at least one ultrasonic transducer to propagate ultrasonic waves and by transmitting at least a second control signal to excite said at least one electromagnetic coil to generate magnetic field lines.

12. The method according to claim 11, further comprising the step of varying a magnitude of said first control signal to vary a transmission power of said propagated ultrasonic waves.

13. The method according to claim 11, further comprising the step of varying a magnitude of said second control signal to vary a magnetic level of the magnetic field lines.

14. The method according to claim 9, further comprising the step of orienting said at least one electromagnetic coil at an angle θ with respect to a horizontal axis of said at least one ultrasonic transducer.

15. The method according to claim 14, wherein θ is greater than or equal to zero degrees and less than or equal to 90 degrees.

16. The method according to claim 9, further including the step of receiving reflected diagnostic data by said at least one ultrasonic transducer.

17. The method according to claim 9, further comprising the step of securing said main operating unit within a carrying case for providing patient mobility during treatment.

18. The method according to claim 9, wherein said step of exciting said at least one electromagnetic coil creates a non-uniform electro magnetic field.

19. A method for ultrasonically and electromagnetically treating tissue and bone defects or injuries, said method comprising:
  securing at least one ultrasonic transducer to a placement band;
  securing at least one electromagnetic coil to said placement band;
  affixing the placement band on a patient such that said at least one ultrasonic transducer is in proximity to a treatment area adjacent to a bone defect or injury;
  exciting said at least one ultrasonic transducer to impinge ultrasonic waves towards said treatment area adjacent to the bone defect or injury;
  exciting said at least one electromagnetic coil to create a modulating force to modulate said ultrasonic waves towards said treatment area adjacent to the bone defect or injury; and
  selectively positioning the at least one electromagnetic coil in different orientations with respect to the ultrasonic transducer to vary the modulating force to modulate said ultrasonic waves.

20. The method according to claim 19, further comprising the step of connecting said at least one ultrasonic transducer and said at least one electromagnetic coil to an operating unit, said operating unit having an internal power source.

21. The method according to claim 19, further including the step of receiving reflected diagnostic data by said at least one ultrasonic transducer.

22. The method according to claim 19, further comprising the step of orienting said at least one electromagnetic coil at an angle θ with respect to a horizontal axis of said at least one ultrasonic transducer; where θ is greater than or equal to zero degrees and less than or equal to 90 degrees.

23. The method according to claim 19, wherein said step of exciting said at least one electromagnetic coil creates a non-uniform modulating force.

24. An apparatus for providing ultrasonic and electromagnetic stimulation to a treatment area adjacent to a bone defect or injury, said apparatus comprising:
  means for generating and propagating an ultrasound wave towards said treatment area adjacent to the bone defect or injury;
  means for generating an electromagnetic field to modulate said ultrasound wave towards said treatment area adjacent to the bone defect or injury;
  means for selectively positioning an electromagnetic coil associated with the electromagnetic field in different orientations with respect to the ultrasound generating means to vary the modulation of said ultrasound wave as it propagates along said treatment area adjacent to the bone defect or injury; and
  control means for controlling one or more properties of said ultrasound wave and said electromagnetic field at respective times.

25. The apparatus according to claim 24, wherein said means for generating an electromagnetic field generates a non-uniform electromagnetic field.

26. The apparatus of claim 24, wherein the control means comprises a controller for varying spatial distribution of the electromagnetic field.

27. The apparatus of claim 24, wherein the control means comprises a controller for varying spatial or temporal generation of the ultrasound wave.

28. The apparatus of claim 24, wherein the control means comprises a controller for varying the spatial distribution of the electromagnetic field, which in turn varies the spatial or temporal generation of the ultrasound wave.

29. The apparatus of claim 24, wherein the properties of the pressure wave are selected from the group consisting of particle displacement, velocity, acceleration, and pressure.

30. A treatment assembly for providing ultrasonic and electromagnetic stimulation to a treatment area adjacent to a bone defect or injury, said assembly comprising:
  at least one ultrasonic transducer assembly having at least one ultrasonic transducer;
  at least one electromagnetic coil assembly having at least one electromagnetic coil operatively associated with said at least one ultrasonic transducer assembly;
  a placement module configured to be worn by a patient, said placement module being configured to receive said at least one ultrasonic transducer assembly and said at least one electromagnetic coil assembly such that when said placement module is worn said at least one ultrasonic transducer and said at least one electromagnetic coil are positioned to provide energy toward said treatment area adjacent to a bone defect or injury, wherein either said at least one ultrasonic transducer or said at least one electromagnetic coil can be selectively positioned relative to the other to vary the amount of modulation of the energy along said treatment area adjacent to said bone defect or injury; and
  a main operating unit for providing at least one driving signal to said at least one ultrasonic transducer assembly for driving said at least one ultrasonic transducer and said at least one electromagnetic coil to provide ultrasonic and electromagnetic stimulation to said treatment area adjacent to the bone defect or injury.

31. A method for ultrasonically and electromagnetically treating tissue and bone defects or injuries, said method comprising:
  providing a main operating unit having an internal power source coupled to at least one ultrasonic transducer assembly and at least one electromagnetic coil assembly, said at least one ultrasonic transducer assembly includes at least one ultrasonic transducer, said at least one electromagnetic coil assembly includes at least one electromagnetic coil;

providing a placement module configured to receive said at least one ultrasonic transducer assembly and said at least one electromagnetic coil assembly such that when said placement module is secured to a patient's body said at least one ultrasonic transducer and said at least one electromagnetic coil are positioned to provide energy towards said treatment area adjacent to a bone defect or injury, wherein either said at least one ultrasonic transducer or said at least one electromagnetic coil can be selectively positioned relative to the other to vary the amount of modulation of the energy;

exciting said at least one ultrasonic transduce to impinge ultrasonic waves towards the treatment area adjacent to the bone defect or injury; and exciting said at least one electromagnetic coil to create an electromagnetic field towards the treatment area adjacent to the bone defect or injury.

32. A method for ultrasonically and electromagnetically treating tissue and bone defects or injuries, said method comprising;

securing at least one ultrasonic transducer to a placement band;

securing at least one electromagnetic coil to said placement band;

affixing the placement band on a patient such that said at least one ultrasonic transducer is in proximity to said treatment area adjacent to a bone defect or injury;

exciting said at least one ultrasonic transducer to impinge ultrasonic waves towards said treatment area adjacent to the bone defect or injury;

exciting said at least one electromagnetic coil to create a modulating force to modulate said ultrasonic waves towards the treatment area adjacent to the bone defect or injury; and selectively positioning either said at least one ultrasonic transducer or said at least one electromagnetic coil relative to the other to vary the amount of modulation of said ultrasonic waves.

* * * * *